United States Patent
Fujino et al.

(10) Patent No.: US 9,596,987 B2
(45) Date of Patent: Mar. 21, 2017

(54) OPHTHALMOLOGIC IMAGING APPARATUS

(71) Applicant: KABUSHIKI KAISHA TOPCON, Itabashi-ku (JP)

(72) Inventors: Makoto Fujino, Itabashi-ku (JP); Hisashi Tsukada, Hachioji (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 14/909,376

(22) PCT Filed: Jul. 25, 2014

(86) PCT No.: PCT/JP2014/069658
§ 371 (c)(1),
(2) Date: Feb. 1, 2016

(87) PCT Pub. No.: WO2015/019867
PCT Pub. Date: Feb. 12, 2015

(65) Prior Publication Data
US 2016/0198951 A1 Jul. 14, 2016

(30) Foreign Application Priority Data
Aug. 8, 2013 (JP) .................. 2013-165637

(51) Int. Cl.
*A61B 3/14* (2006.01)
*A61B 3/00* (2006.01)
(Continued)

(52) U.S. Cl.
CPC ............. *A61B 3/12* (2013.01); *A61B 3/0025* (2013.01); *A61B 3/0041* (2013.01);
(Continued)

(58) Field of Classification Search
USPC .................................. 351/200–246
See application file for complete search history.

(56) References Cited

U.S. PATENT DOCUMENTS 6,377,349 B1 4/2002 Fercher
2003/0223038 A1 12/2003 Alster et al.
(Continued)

FOREIGN PATENT DOCUMENTS

JP 8-10223 A 1/1996
JP 9-276232 A 10/1997
(Continued)

OTHER PUBLICATIONS

International Search Report Issued Oct. 28, 2014 in PCT/JP2014/069658 Filed Jul. 25, 2014.
PCT International Preliminary Report on Patentability issued Feb. 9, 2016 in PCT/JP2014/069658, 1 page.
PCT Written Opinion of the International Searching Authority issued Oct. 28, 2014 in PCT/JP2014/069658 with English translation, 10 pages.

*Primary Examiner* — Mohammed Hasan
(74) *Attorney, Agent, or Firm* — Oblon, McClelland, Maier & Neustadt, L.L.P.

(57) ABSTRACT

An ophthalmologic imaging apparatus includes: an optical system that divides light into measurement light and reference light, causes the measurement light returning from a subject's eye to interfere with the reference light, and detects interference light resulting therefrom; a processor that processes a detection result of the interference light to generate test data indicating the state of the subject's eye; an output unit that outputs the test data; an interface used to make the setting of a predetermined item related to the optical system and the processor; a storage that stores setting information indicating the content of the setting made through the interface; and a controller that controls the optical system and the processor based on the content of the setting indicated by the setting information in each of a plurality of tests performed until the setting information is changed or deleted.

21 Claims, 4 Drawing Sheets

(51) Int. Cl.
*A61B 3/12* (2006.01)
*A61B 3/10* (2006.01)
*A61B 5/00* (2006.01)
*G02B 27/14* (2006.01)

(52) U.S. Cl.
CPC ............ *A61B 3/0091* (2013.01); *A61B 3/102* (2013.01); *A61B 3/1005* (2013.01); *A61B 3/1025* (2013.01); *A61B 3/14* (2013.01); *A61B 5/0013* (2013.01); *G02B 27/141* (2013.01)

(56) References Cited

U.S. PATENT DOCUMENTS

| | | |
|---|---|---|
| 2005/0122477 A1 | 6/2005 | Alster et al. |
| 2006/0100528 A1 | 5/2006 | Chan et al. |
| 2009/0244482 A1 | 10/2009 | Elsner et al. |
| 2009/0244485 A1 | 10/2009 | Walsh et al. |
| 2010/0128221 A1 | 5/2010 | Muller et al. |
| 2013/0201449 A1 | 8/2013 | Walsh et al. |
| 2013/0215388 A1* | 8/2013 | Imamura ............... G06T 7/0012 351/206 |
| 2015/0138503 A1 | 5/2015 | Walsh et al. |
| 2016/0120405 A1* | 5/2016 | Tokuda ................ A61B 3/0075 351/208 |

FOREIGN PATENT DOCUMENTS

| | | |
|---|---|---|
| JP | 11-325849 A | 11/1999 |
| JP | 2002-139421 A | 5/2002 |
| JP | 2005-517482 A | 6/2005 |
| JP | 2006-153838 A | 6/2006 |
| JP | 2007-24677 A | 2/2007 |
| JP | 2008-73099 A | 4/2008 |
| JP | 2008-259544 A | 10/2008 |
| JP | 2009-11381 A | 1/2009 |
| JP | 2009-538697 A | 11/2009 |
| JP | 2011-515194 A | 5/2011 |

\* cited by examiner

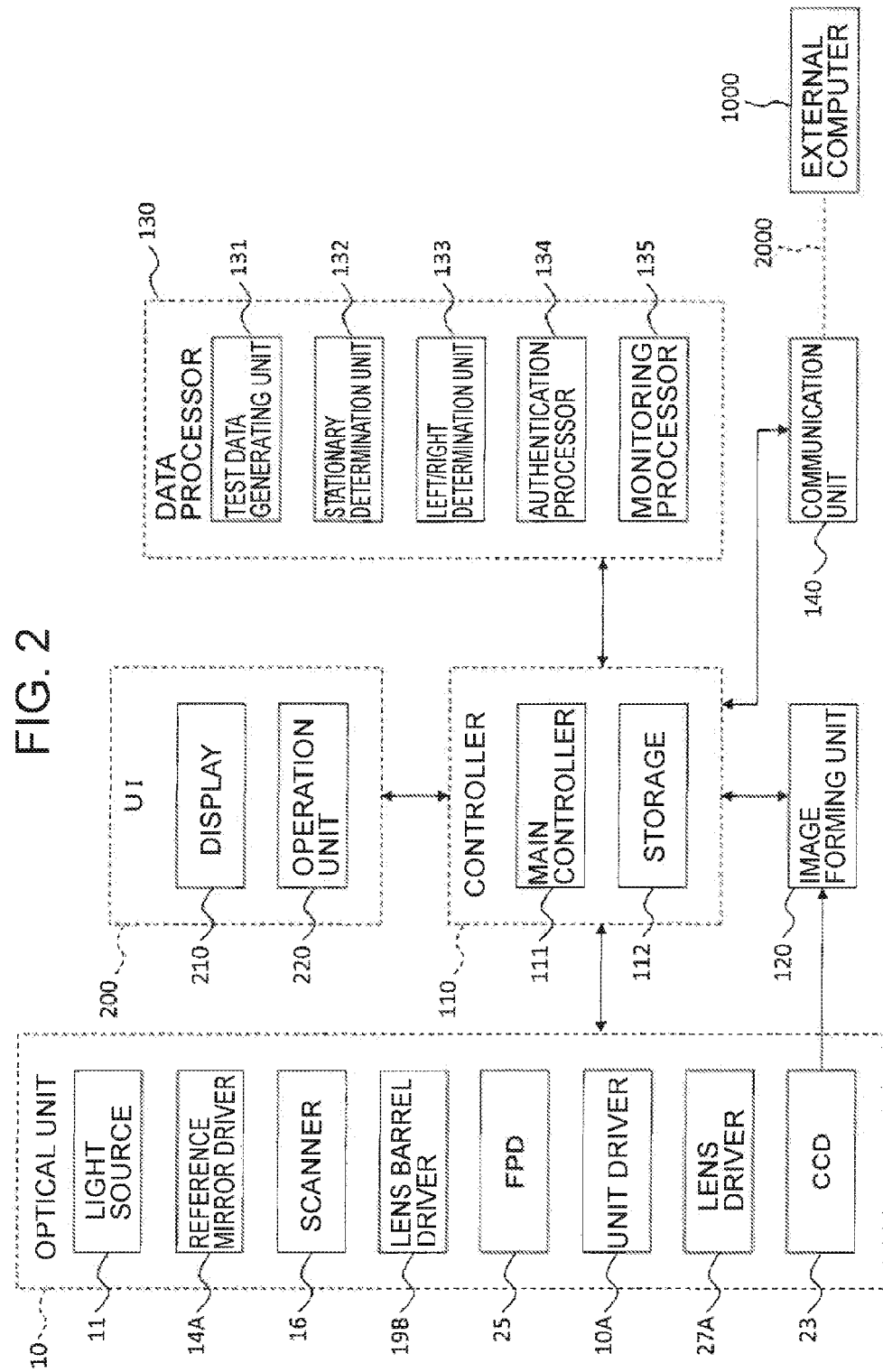

OPHTHALMOLOGIC IMAGING APPARATUS

TECHNICAL FIELD

Embodiments described herein relate generally to an ophthalmologic imaging apparatus that uses optical coherence tomography (OCT) to acquire an image of a subject's eye.

BACKGROUND ART

In recent years, optical coherence tomography (OCT) has been drawing attention. The OCT creates an image representing the exterior or interior structure of an object to be measured using light beams from a laser light source or the like. Unlike X-ray computed tomography (CT), the OCT is not invasive on the human body, and therefore is expected to be applied to the medical field and the biological field, in particular. For example, in the opthalmological field, apparatuses for forming images of the fundus oculi or the cornea have been in practical use.

Patent Document 1 discloses a device using Fourier-domain OCT or frequency-domain OCT. This device irradiates an object to be measured with a beam of low-coherence light, and superimposes the light reflected from the object on reference light to generate interference light. The device then obtains the spectral intensity distribution of the interference light, and applies Fourier transform thereto to acquire an image of the morphology of the object to be measured in the depth direction (z direction). The device includes a galvanometer mirror configured to scan a light beam (measurement light) in a direction (x direction) perpendicular to the z direction, thereby forming an image of a desired area of the object to be measured. The image formed by the device is a two-dimensional cross-sectional image in the depth direction (z direction), taken along the scanning direction (x direction) of the light beam. Such technique using a spectrometer is called "spectral-domain".

Patent Document 2 discloses a technology, in which measurement light is scanned in the horizontal direction (x direction) and the vertical direction (y-direction) to thereby form a plurality of two-dimensional cross-sectional images in the horizontal direction. Based on the cross-sectional images, three-dimensional cross-section information is obtained for a measurement range. As the three-dimensional imaging, for example, there are a method of arranging a plurality of cross-sectional images in the vertical direction (referred to as "stack data", etc.), a method of performing rendering on volume data (voxel data) based on the stack data to thereby form a three-dimensional image, and the like.

Patent Documents 3 and 4 disclose OCT devices of other types. Patent Document 3 discloses an OCT device, which scans (sweeps) the wavelengths of light irradiated to the object to be measured, and sequentially detects interference light obtained by superimposing reflected light of each wavelength on reference light to acquire spectral intensity distribution. The device applies Fourier transform to the spectral intensity distribution to form an image of the morphology of the object to be measured. Such an OCT device is called swept-source OCT. The swept-source OCT is a type of Fourier-domain OCT.

Patent Document 4 discloses an OCT device, which irradiates light beams having a predetermined diameter to an object to be measured, and analyzes the components of interference light obtained by superimposing the reflected light on reference light. Thereby, the device captures an image of the object to be measured in a cross-section perpendicular to the traveling direction of the light. Such an OCT device is called full-field OCT or en-face OCT.

Patent Document 5 discloses a configuration in which OCT is applied to the ophthalmologic field. Incidentally, before the application of OCT, a fundus camera, a slit lamp, a scanning laser opthalmoscope (SLO), or the like has been used as a device for observing the subject's eye (see, for example, Patent Documents 6, 7, and 8). The fundus camera is a device that irradiates the subject's eye with illumination light and receives the light reflected from the fundus to thereby capture an image of the fundus. The slit lamp is a device that cuts out an optical section of the cornea using a slit light to thereby acquire an image of the cross-section of the cornea. The SLO is a device that scans the fundus with a laser beam, and detects its reflected light with a high-sensitivity element such as a photomultiplier tube for imaging the morphology of the fundus surface.

The devices using OCT offer advantages with respect to the fundus camera in that they can acquire high-resolution images, and also that they can obtain cross-sectional images as well as three-dimensional images.

As described above, the devices using OCT can be used for the observation of different parts of the eye, and are capable of acquiring high-resolution images. Therefore, the OCT devices have been applied to a variety of ophthalmic diseases. For example, there has been a known device, which is made of a combination of an OCT device and a subjective visual acuity test device, and provides materials for the diagnosis of maculopathy and glaucoma (see Patent Document 9).

[Patent Document 1] Japanese Unexamined Patent Application Publication No. Hei 11-325849
[Patent Document 2] Japanese Unexamined Patent Application Publication No. 2002-139421
[Patent Document 3] Japanese Unexamined Patent Application Publication No. 2007-24677
[Patent Document 4] Japanese Unexamined Patent Application Publication No. 2006-153838
[Patent Document 5] Japanese Unexamined Patent Application Publication No. 2008-73099
[Patent Document 6] Japanese Unexamined Patent Application Publication No. Hei 9-276232
[Patent Document 7] Japanese Unexamined Patent Application Publication No. 2008-259544
[Patent Document 8] Japanese Unexamined Patent Application Publication No. 2009-11381
[Patent Document 9] Japanese Unexamined Patent Application Publication (Translation of PCT Application) No. 2011-515194

SUMMARY OF THE INVENTION

Problems to be Solved by the Invention

Depending on the type of ophthalmic diseases, it is desirable to check the condition frequently. For example, in the case of age-related macular degeneration, the drug administration is performed according to the condition. Accordingly, it is preferable to manage the medication timing along with frequent checks of the condition. Besides, considering that the drugs are relatively expensive, it is also desirable from the patient's point of view to manage the medication such that the minimum necessary dose is administered at an appropriate timing.

However, it has been required for the patients to have frequent hospital visits to realize the desired management as described above. On the other hand, diseases such as age-related macular degeneration and glaucoma require a long-term management. It is obviously a heavy burden for the patients to continue routine hospital visits over a long period of time.

One approach to solve this problem may be to check the conditions of the disease (i.e., perform OCT measurement) at home or the like (in a location other than medical institutions in general). However, it is necessary to make various settings to perform a test by using the OCT device. Examples of the settings include setting of a site (optic disc, macula, etc.) to be imaged, setting of a scan pattern, setting of a focus position (measurement depth), setting of diopter correction according to the visual acuity of the subject's eye, settings as to whether the left eye or the right eye is to be tested, selection of an analysis process (such as fundus thickness analysis, drusen analysis, etc.).

To make the proper setting of the OCT device, users are required to be trained and explained about the device, and also to acquire a certain degree of experience. That is, it has been difficult for those who do not have such knowledge and experience (including those who do not have much knowledge and experience) to carry out a proper test by using the OCT device.

It is therefore an object of the present invention to provide an ophthalmologic imaging apparatus that enables even those having no or little knowledge and experience about using the apparatus to easily perform a test.

Means of Solving the Problems

An ophthalmologic imaging apparatus of an embodiment includes: an optical system configured to divide light from a light source into measurement light and reference light, cause the measurement light returning from a subject's eye to interfere with the reference light, and detect interference light resulting therefrom; a processor configured to process a detection result of the interference light obtained by the optical system to generate test data indicating the state of the subject's eye; an output unit configured to output the test data generated by the processor; an interface used to make the setting of a predetermined item related to the optical system and the processor; a storage configured to store setting information indicating the content of the setting made through the interface; and a controller configured to control the optical system and the processor based on the content of the setting indicated by the setting information in each of a plurality of tests performed until the setting information is changed or deleted.

Effects of the Invention

According to the present invention, even those having no or little knowledge and experience about using the apparatus can easily perform a test.

BRIEF DESCRIPTION OF THE DRAWINGS

FIG. 2 is a schematic diagram illustrating an example of the configuration of the ophthalmologic imaging apparatus according to an embodiment.

MODES FOR CARRYING OUT THE INVENTION

Figure 1:
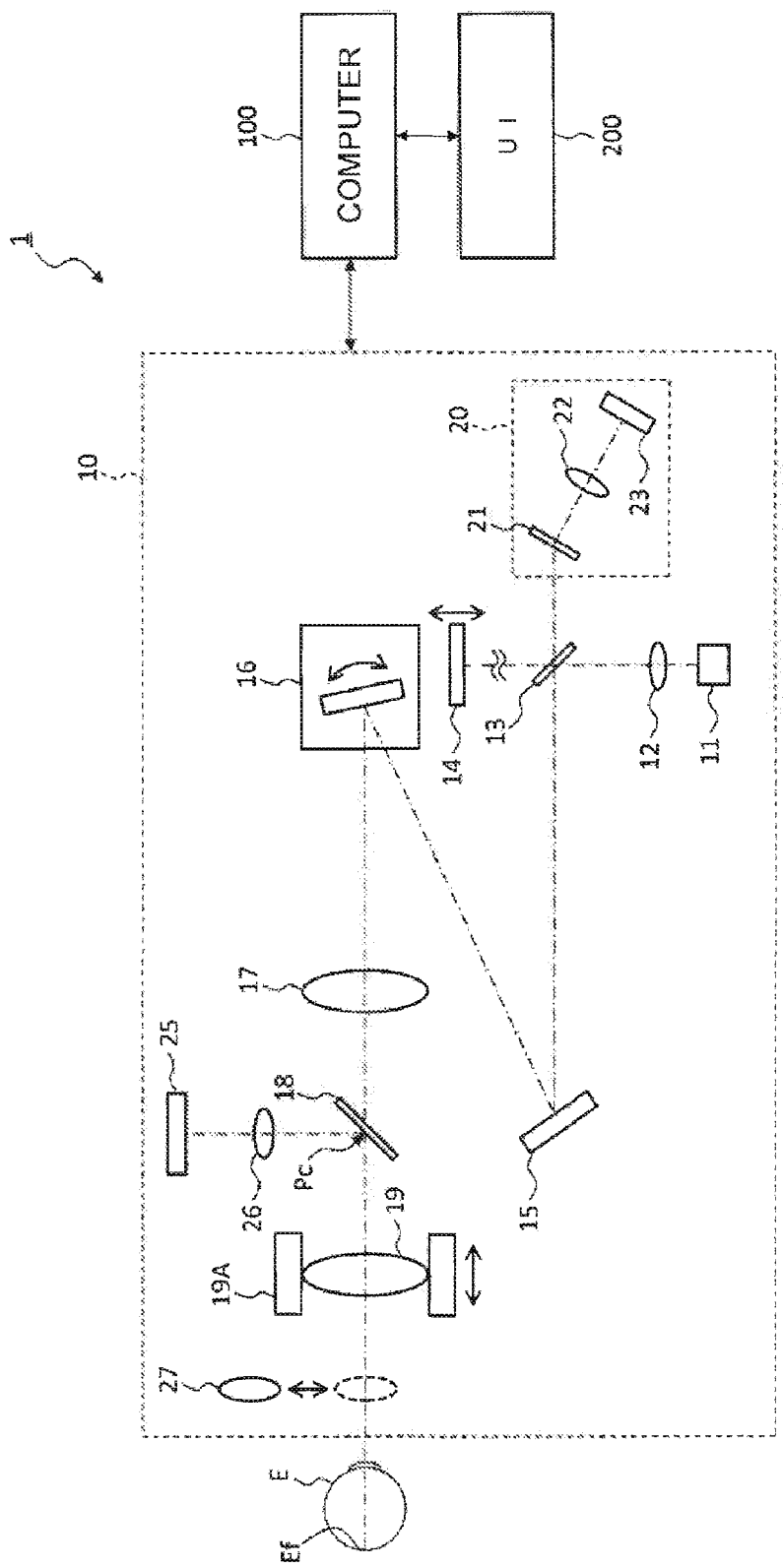
FIG. 1 is a schematic diagram illustrating an example of the configuration of an ophthalmologic imaging apparatus according to an embodiment.

Referring now to the drawings, a detailed description is given of an ophthalmologic imaging apparatus according to embodiments of the present invention. The ophthalmologic imaging apparatus of the present invention creates a cross-sectional image of the fundus of an eye using OCT imaging. Hereinafter, the image acquired through OCT may sometimes be referred to as "OCT image". In addition, measurement for forming the OCT image may sometimes be referred to as "OCT measurement". The contents of the documents cited herein may be incorporated by reference into the embodiment as appropriate.

While the following embodiment is described as using spectral-domain OCT, for the ophthalmologic imaging apparatus using other types of OCT, the embodiment can be applied to other types of OCT. Further, the apparatus of the embodiment may have an imaging function other than OCT. As an example of the additional imaging function may be cited the function of capturing a front image of the anterior segment and/or fundus of an eye (see, for example, Patent Document 5).

[Configuration]

Described below is the configuration of an ophthalmologic imaging apparatus according to an embodiment. As illustrated in FIG. 1, an ophthalmologic imaging apparatus 1 includes an optical unit 10, a computer 100, and a user interface (UI) 200.

The optical unit 10, the computer 100, and the user interface 200 may be integrated (i.e., accommodated in a single housing). Alternatively, they may be located separately in two or more housings. In this case, part of the ophthalmologic imaging apparatus may be provided to another apparatus. For example, part or whole of the computer 100 can be provided to a personal computer or a portable terminal (a tablet computer, a cellular phone, a smart phone, etc.). In addition, part or whole of the user interface 200 can be provided to a personal computer, a portable terminal, a television receiver, a smart TV, or the like.

(Optical Unit 10)

The optical unit 10 includes an optical system for performing OCT measurement and a mechanism for driving a predetermined optical element. The optical system splits light from a light source 11 into measurement light and reference light, and causes the measurement light returning from the subject's eye E to interfere with the reference light, thereby detecting the interference light. The optical system has the same configuration as a conventional spectral-domain OCT device. That is, the optical system is configured to divide low-coherence light (broad band light) into reference light and measurement light, causes the measurement light having passed through the subject's eye E to interfere with the reference light having propagated through the reference optical path to generate interference light, and detect spectral components of the interference light. The detection result of the spectral components (detection signal) is sent to the computer 100.

If swept-source OCT is used, the low-coherence light source is replaced by a wavelength swept light source (wavelength tunable light source), and an optical member is not provided for spectral decomposition of interference light. In general, a known technology can be arbitrarily applied to the configuration of the optical unit 10 according to the type of OCT.

The light source 11 outputs wide-band low-coherence light. The low-coherence light includes, for example, wavelengths in the near-infrared region (about 800 nm to 900 nm), and has a temporal coherence length of about several tens of micrometers. Incidentally, the low-coherence light may be near infrared light of wavelengths invisible to the human eye, for example, with a center wavelength of about 1040 nm to 1060 nm.

The light source 11 includes a light output device, such as a super luminescent diode (SLD), a light-emitting diode (LED), or a semiconductor optical amplifier (SOA).

The low-coherence light output from the light source 11 is collimated into a parallel light flux by a collimator lens 12 and guided to a beam splitter 13. The beam splitter 13 is, for example, a half mirror that reflects a predetermined proportion of light and transmits the rest. The beam splitter 13 splits the parallel light flux into measurement light and reference light.

The measurement light is light that is irradiated to the subject's eye E (also referred to as signal light). A group of optical elements which forms the optical path of the measurement light (measurement optical path) is referred to as measurement arm (also referred to as sample arm). The reference light serves as a reference to extract information contained in return light of the measurement light as an interference signal. A group of optical elements which forms the optical path of the reference light (reference optical path) is referred to as reference arm.

The beam splitter 13 is arranged at one end of the reference optical path, and a reference mirror 14 is arranged at the other end. The reference light formed of components having transmitted through the beam splitter 13 is reflected by the reference mirror 14, and returned to the beam splitter 13.

By a reference mirror driver 14A illustrated in FIG. 2, the reference mirror 14 is moved along the traveling direction of the reference light. Thereby, the length of the reference optical path is changed. The reference mirror driver 14A functions to relatively change the length of the measurement optical path and the length of the reference optical path to thereby change the depth position where the intensity of interference between the measurement light and the reference light becomes maximum. The reference mirror 14 and the reference mirror driver 14A are an example of the maximum interference depth change unit. Besides, the reference mirror driver 14A is an example of the third driver.

In this embodiment, a configuration is employed in which the length of the reference optical path is changed, instead of or in addition to this configuration, there may be provided a configuration to change the length of the measurement optical path. The length of the measurement optical path can be changed by, for example, a corner cube that reflects incident measurement light in a direction opposite to the incident direction and a mechanism for moving the corner cube in the incident direction and the reflection direction.

The measurement light formed of components reflected by the beam splitter 13 is deflected by a fixed mirror 15 arranged to be inclined with respect to the measurement optical path, and is directed to a scanner 16. The scanner 16 is, for example, a two-axis optical scanner. This means that the scanner 16 is configured to be capable of two-dimensionally deflecting the measurement light. The scanner 16 is, for example, a mirror scanner including two mirrors which can be polarized in directions perpendicular to each other.

The mirror scanner is configured as, for example, a micro-electro-mechanical systems (MEMS). As another example, the scanner 16 may be formed by using one mirror scanner and a rotary prism.

The measurement light output from the scanner 16 is two-dimensionally deflected collimated light. This measurement light is focused by a relay lens 17, and aerially forms an image in a plane (fundus conjugate plane) Pc conjugate to the fundus Ef. Further, the measurement light is once again focused by an objective lens 19 having the function of a focusing lens, and is incident on the subject's eye E. Incidentally, an optical element (dichroic mirror 18) arranged in the fundus conjugate plane Pc is described later. Besides, when a diopter correction lens 27 (described later) is located in the measurement optical path, after having passed through the objective lens 19, the measurement light is refracted by the diopter correction lens 27 and incident on the subject's eye E.

The objective lens 19 and a lens barrel 19A are moved along the measurement optical path by a lens barrel driver 19B illustrated in FIG. 2. The objective lens 19 and the lens barrel 19A are moved in the optical axis direction according to the refractive power of the subject's eye E. Thus, the fundus conjugate plane Pc is located in a position conjugate to the fundus Ef. As a result, the measurement light is projected onto the fundus Ef as a spot light. The objective lens 19 and the lens barrel driver 19B are an example of the focus position change unit that changes a focus position of the measurement light with respect to the subject's eye E. The lens barrel driver 19B is an example of the first driver that moves the objective lens 19 (focusing lens). Incidentally, a focusing lens may be provided additionally to the objective lens 19.

As with the focusing lens, the diopter correction lens 27 is configured to change the focus position of the measurement light with respect to the subject's eye E. The diopter correction lens 27 is an optical element arranged in the measurement optical path to, for example, deal with the subject's eye with an extreme refractive power like high myopia. The diopter correction lens 27 is inserted into/removed from the measurement optical path by a lens driver 27A illustrated in FIG. 2. The diopter correction lens 27 and the lens driver 27A are an example of the focus position change unit for changing the focus position of the measurement light with respect to the subject's eye E. In addition, the lens driver 27A is an example of the second driver for moving the diopter correction lens 27.

Note that the focus position change unit may include a plurality of diopter correction lenses with different powers and a second driver configured to selectively arrange arbitrary one of the diopter correction lenses on the measurement optical path. Besides, it is also possible to use an optical element having a variable refractive power like, for example, Alvarez lens. Such an optical element for diopter correction is located between the subject's eye E and the objective lens 19, for example.

The measurement light irradiated to the fundus Ef is scattered (and reflected) at various depth positions of the fundus Ef. The backscattered light (return light) of the measurement light from the fundus Ef travels the same path in the reverse direction and is guided to the beam splitter 13.

The beam splitter 13 causes the return light of the measurement light to interfere with the reference light having passed through the reference optical path. At this time, components of the return light which have traveled about the same distance as the length of the reference optical path, i.e., only the backscattered light from the range within the coherence length to the length of the reference optical path, substantially interfere with the reference light. The interference light generated through the beam splitter 13 is guided to a spectroscope 20. The interference light incident on the spectroscope 20 is dispersed (spectrally resolved) by a diffraction grating 21, and irradiated to a light receiving surface of a CCD image sensor 23 through a lens 22. Although FIG. 1 illustrates a transmissive diffraction grating as the diffraction grating 21, the diffraction grating 21 may be formed using a spectral element of other forms, such as, for example, a reflection diffraction grating.

The CCD image sensor 23 is, for example, a line sensor or an area sensor. The CCD image sensor 23 detects each spectral component of the dispersed interference light, and converts it to electric charges. The CCD image sensor 23 accumulates the electric charges to generate a detection signal, and sends it to the computer 100.

As described above, the dichroic mirror 18 is arranged to be inclined in a position corresponding to the fundus conjugate plane Pc of the measurement optical path. The dichroic mirror 18 is configured to transmit measurement light in the near-infrared band therethrough and reflect light in the visible band.

Arranged in an optical path branched from the measurement optical path via the dichroic mirror 18 are a flat panel display (FPD) 25 and a lens 26. The flat panel display 25 displays information under the control of a controller 110. As an example of the information displayed on the flat panel display 25 may be cited various types of visual targets that are presented to the subject's eye E. Examples of the visual targets include optotypes (Landolt rings) for subjective visual acuity test, a fixation target to help the subject's eye E to fixate, and the like.

The flat panel display 25 is located in a position conjugate to the fundus conjugate plane Pc (i.e., a position conjugate to the fundus Ef) through the lens 26. The flat panel display 25 may be, for example, a liquid crystal display (LCD) or an organic electroluminescence display (OELD).

Visible light output from the flat panel display 25 is reflected to the dichroic mirror 18 through the lens 26. The visible light is incident on the subject's eye E through the objective lens 19, and reaches the fundus Ef. Thereby, an image (e.g., visual target image) based on the visible light is projected onto the fundus Ef.

An optical element such as a half mirror may be provided instead of the dichroic mirror 18. It is also possible to provide a reflection mirror configured to be insertable into/removable from the measurement optical path. If the dichroic mirror 18 and a half mirror are provided, the projection of a visual target can be performed simultaneously with OCT measurement. On the other hand, when a reflection mirror is provided, OCT measurement and the projection of a visual target are performed at different timings.

While this embodiment employs a Michelson interferometer, it is possible to use any type of interferometer, such as, for example, a Mach-Zehnder interferometer. Further, in place of the CCD image sensor, it is possible to use a light receiving element of another form, such as, for example, a complementary metal-oxide semiconductor (CMOS) image sensor.

In this embodiment, the light reflected by the beam splitter 13 is used as the measurement light, and the light having transmitted through it is used as the reference light. Meanwhile, on the contrary, the light reflected by the beam splitter 13 may be used as the reference light, and the light having transmitted through it may be used as the measurement light. In this case, the arrangement of the measurement arm and the reference arm is reversed from FIG. 1.

There may be provided a member for converting the properties of the measurement light and/or the reference light. For example, an optical attenuator and a polarization adjuster (polarization controller) may be provided in the reference optical path. The optical attenuator adjusts the amount of the reference light under the control of the computer 100. The optical attenuator includes, for example, a neutral density filter and a mechanism for inserting/removing it into/from the reference optical path. The polarization adjuster adjusts the polarization state of the reference light under the control of the computer 100. The polarization adjuster includes, for example, a polarizing plate arranged on the reference optical path, and a mechanism for rotating it. These are used to adjust the interference intensity of the return light of the measurement light and the reference light.

A front image acquisition optical system may be provided to capture a front image of the subject's eye E. The front image is an image of the anterior segment and the fundus Ef of the eye. The front image acquisition optical system forms an optical path branched from the measurement optical path, and includes, for example, an illumination optical system and an imaging optical system similar to those of the conventional fundus camera. The illumination optical system irradiates illumination light consisting of (near) infrared light or visible light to the subject's eye E. The imaging optical system detects the illumination light returning from the subject's eye E (reflected light). The imaging optical system shares a common focusing lens (the objective lens 19, the diopter correction lens 27, etc.) with the measurement optical path, and/or includes a focusing lens separately from the measurement optical path. As another example of the front image acquisition optical system may be cited the same optical system as the conventional SLO.

If there is the front image acquisition optical system, it is possible to further provide an alignment optical system as in the conventional fundus camera. The alignment optical system is configured to form an optical path branched from the measurement optical path, and generates a visual target (alignment visual target) to align the optical system of the apparatus with the subject's eye E. The alignment is performed in a direction (referred to as xy direction) along a plane perpendicular to the measurement optical path (the optical axis of the objective lens 19). Although not illustrated, the alignment optical system generates two alignment light fluxes by a two-hole aperture from light fluxes output from an alignment light source (LED, etc.). The two alignment light fluxes are guided to the measurement optical path via a beam splitter arranged to be inclined with respect to the measurement optical path. Thus, the alignment light fluxes are projected onto the cornea of the subject's eye E. The alignment light fluxes reflected from the cornea are detected by the image sensor of the front image acquisition optical system.

If there is the alignment optical system, automatic alignment can be performed. Specifically, a data processor 130 of the computer 100 analyzes a signal received from the image sensor of the front image acquisition optical system, and specifies the positions of two alignment visual target images. Further, based on the positions of the two alignment visual target images specified, the controller 110 moves the optical unit 10 in the xy direction such that two cornea reflection light beams are projected as being overlapped each other onto a predetermined position (e.g., the center position) on the light receiving surface of the image sensor. Incidentally, a unit driver 10A is provided to move the optical unit 10.

If there is the front image acquisition optical system, it is possible to further provide a focusing optical system as in the conventional fundus camera. The focusing optical system is configured to form an optical path branched from the measurement optical path, and generates a visual target (split target) for focusing on the fundus Ef. Although not illustrated, the focusing optical system generates two focusing light fluxes by a split target plate from light fluxes output from a focusing light source (LED, etc.). The two focusing light fluxes are guided to the measurement optical path via a reflective member arranged to be inclined with respect to the measurement optical path. Thus, the focusing light fluxes are projected onto the fundus Ef. The focusing light fluxes reflected from the fundus are detected by the image sensor of the front image acquisition optical system.

If there is the focusing optical system, automatic focusing can be performed. Specifically, the data processor 130 of the computer 100 analyzes a signal received from the image sensor of the front image acquisition optical system, and specifies the positions of two split visual target images. Further, based on the positions of the two split visual target images specified, the controller 110 controls the focusing lens as well as the movement of the focusing optical system (e.g., the movement of the objective lens 19) such that two light fluxes reflected from the fundus are projected on a straight line on the light receiving surface of the image sensor.

If there is the front image acquisition optical system, it possible to perform automatic tracking. In automatic tracking, the optical unit 10 moves along the movement of the subject's eye E. To perform automatic tracking, alignment and focusing are performed in advance. The automatic tracking is performed, for example, in the following manner; First, the front image acquisition optical system captures a moving image of the subject's eye E. The data processor 130 sequentially analyzes frames of the moving image to monitor the movement (positional change) of the subject's eye E. The controller 110 controls the unit driver 10A to move the optical unit 10 according to the position of the subject's eye E successively acquired. Thereby, the optical unit 10 can follow the movement of the subject's eye E in real time. Thus, it is possible to maintain a suitable positional relationship with proper alignment and focus.

(Control System and Data Processing System)

Described below are the control system and the data processing system of the ophthalmologic imaging apparatus 1 according to the embodiment. FIG. 2 illustrates an example of the configuration of the control system and the data processing system.

The control system and the data processing system are configured centered on the computer 100. The computer 100 includes a microprocessor, RAM, ROM, a hard disk drive, a communication interface, and the like. The computer 100 stores computer programs for implementing various types of processing on the ophthalmologic imaging apparatus 1 in a storage device such as a hard disk drive. The computer 100 may have a dedicated circuit board to perform specific processing. For example, the computer 100 may be provided with a circuit board for implementing the process of forming an OCT image.

(User Interface 200)

The user interface 200 is connected to the computer 100. The user interface 200 includes a display 210 and an operation unit 220. The display 210 includes a display device such as a flat panel display or the like. The operation unit 220 includes buttons, keys, a joystick, an operation device such as an operation panel in the outside and the housing of the ophthalmologic imaging apparatus 1. If the computer 100 includes a personal computer, the operation unit 220 may include an operation device of the personal computer (a mouse, a keyboard, a track pad, buttons, etc.).

The display 210 and the operation unit 220 need not necessarily be configured as separate devices, and they may be a device having a display function integrated with an operation function, like, for example, a touch panel. In this case, the operation unit 220 includes the touch panel and a computer program. The content of operation performed on the operation unit 220 is input to the controller 110 as an electrical signal. Further, operation or data input may be performed by using a graphical user interface (GUI) displayed on the display 210 and the operation unit 220.

(Controller 110)

The controller 110 is provided to the computer 100. The controller 110 includes a microprocessor, RAM, ROM, a hard disk drive, and the like. The controller 110 includes a main controller 111 and a storage 112.

(Main Controller 111)

The main controller 111 controls each unit in the ophthalmologic imaging apparatus 1. For example, the main controller 111 controls the unit driver 10A, the light source 11, the reference mirror driver 14A, the scanner 16, the lens barrel driver 19B, the CCD (image sensor) 23, the flat panel display 25, the display 210, the data processor 130, and a communication unit 140.

The unit driver 10A has a mechanism for moving the optical unit 10 in a direction (z direction) along the measurement optical path (the optical axis of the objective lens 19) and a direction (xy direction) along a plane perpendicular to the z direction. The reference mirror driver 14A moves the reference mirror 14 along the reference optical path. The lens barrel driver 19B moves the objective lens 19 and the lens barrel 19A along the measurement optical path. The lens driver 27A inserts/removes the diopter correction lens 27 into/from the measurement optical path. Alternatively, the lens driver 27A selectively arranges a plurality of diopter correction lenses on the measurement optical path (the lens driver 27A may remove all the diopter correction lenses from the measurement optical path).

(Storage 112)

The storage 112 stores a variety of data. The storage 112 also stores various types of computer programs and data for operating the ophthalmologic imaging apparatus 1. The data stored in the storage 112 includes data obtained by the ophthalmologic imaging apparatus 1, and data stored in advance.

Examples of the data obtained by the ophthalmologic imaging apparatus 1 include image data of an OCT image, test data, image data of a front image, and the like. The test data includes data indicating the state of the subject's eye (described in detail later), which is generated by processing the detection result of the interference light obtained by the optical unit 10. Examples of the data stored in the storage 112 in advance include setting information and authorized user authentication information.

(Setting Information)

The setting information indicates the content of the setting of a predetermined item related to the optical unit 10 and the data processor 130. The setting information includes the content of the setting related to, for example, at least one of the following items: (1) fixation position; (2) scan pattern; (3) focus position; (4) diopter correction; (5) maximum interference depth; (6) and analysis.

(1) The "fixation position" indicates the direction in which the subject's eye E is made to fixate, i.e., a site of the subject's eye E subjected to OCT measurement. Examples of the fixation position include a fixation position for OCT measurement of the macula and its periphery, a fixation position for OCT measurement of the optic disc and its periphery, and a fixation position for OCT measurement of the macula, the optic disc, and their peripheries. A fixation position may be set correspondingly to an arbitrary site of the subject's eye E. The fixation position includes, for example, information indicating the display position of the fixation target (the position of pixels) on the flat panel display 25.

(2) The "scan pattern" indicates a pattern along which the projection position of the measurement light is moved with respect to the subject's eye E. Examples of the scan pattern include one or more line scans (horizontal scan, vertical scan), one or more cross-scans, radial scans, circle scans, and the like. To acquire a three-dimensional image (three-dimensional data set), a three-dimensional scan pattern is employed in which a plurality of scan lines are arranged at sufficiently narrow intervals.

(3) The "focus position" indicates focus conditions applied in OCT measurement. The focus position includes, for example, information indicating the position of the objective lens 19.

(4) The "diopter correction" indicates conditions used in diopter correction. Specific examples of the diopter correction include a value indicating the refractive power (visual acuity) of the subject's eye E, use/non-use of a diopter correction lens, a value indicating the refractive power to be applied by the diopter correction lens.

(5) The "maximum interference depth" indicates a depth where the interference intensity of the measurement light and the reference light applied in OCT measurement is the maximum. The maximum interference depth includes, for example, information indicating the position of the reference mirror 14.

(6) The "analysis" indicates the content of processing performed based on data acquired by the optical unit 10, i.e., the type of test data to be acquired. Examples of the analysis include fundus layer thickness analysis, drusen analysis, optic disc shape analysis, and the like. The fundus layer thickness analysis is a process of obtaining the thickness of a predetermined layer tissue (the retina, sub-tissue of the retina, the choroid, the sclera, etc.) of the fundus. The drusen analysis is a process of obtaining the distribution of drusen (mass of waste products) to be used as a diagnostic material for age-related macular degeneration. The optic disc shape analysis is a process of analyzing a cross-sectional image or a three-dimensional image of the fundus to detect a hole (cut, defect site) in the retina, and thereby determining the shape of the optic disc. In the optic disc shape analysis, a tilt of the optic disc (asymmetry of the shape) can be obtained. These analysis processes are described in detail later.

When OCT measurement is performed for both the left and right eyes of the subject, especially when different settings are used for the left and right eyes, setting information for the left eye (left eye setting information) and setting information for the right eye (right eye setting information) may be provided separately.

Further, when two or more subjects share the ophthalmologic imaging apparatus 1, especially when different settings are used for the subjects, setting information may be provided individually for the subjects.

Described below is how to create the setting information. The ophthalmologic imaging apparatus 1 is rented to the subject, and is used at home or the like of the subject. The setting information is created before the apparatus is rented.

A first example of a method of creating the setting information involves the use of the user interface 200 of the ophthalmologic imaging apparatus 1. For example, on a predetermined setting screen displayed on the display 210, the content of the setting of a predetermined item related to the optical unit 10 and the data processor 130 are entered by using the operation unit 220. The main controller 111 creates the setting information including the content of the setting, and stores it in the storage 112. In this case, the user interface 200 functions as an interface.

A second example of a method of creating the setting information involves the use of a computer (e.g., the external computer 1000) connected to the ophthalmologic imaging apparatus 1. The external computer 1000 is a personal computer used by, for example, a doctor. The external computer 1000 is provided with the function (computer program) of creating the setting information. A predetermined setting screen is displayed on the display of the external computer 1000. A doctor or the like enters the content of the setting of a predetermined item related to the optical unit 10 and the data processor 130 by using an operation device (keyboard, mouse, etc.). The external computer 1000 sends the content of the setting through a communication line 2000 (or a cable for direct connection) to the ophthalmologic imaging apparatus 1. The ophthalmologic imaging apparatus 1 receives the content of the setting sent from the external computer 1000 by the communication unit 140. The main controller 111 creates the setting information including the content of the setting received, and stores it in the storage 112. In this case, the communication unit 140 functions as an interface. Incidentally, while, in this example, the content of the setting is entered and sent to the apparatus on the external computer 1000, the process up to the creation of setting information may be performed by the external computer 1000.

The setting information is created with reference to test results and test conditions of the subject's eye E, the disease name (type of data to be diagnostic material), and the like. For example, the fixation position is set with reference to a fixation position used in the past OCT measurement, and the disease name. The scan pattern is set with reference to a scan pattern used in the past OCT measurement, and the disease name. The focus position is set with reference to a focus position used in the past OCT measurement. The diopter correction is set with reference to whether a diopter correction lens is used in the past OCT measurement, or the visual acuity and the refractive power obtained in the past test. The maximum interference depth is set with reference to a maximum interference depth used in the past OCT measurement. The analysis is set with reference to the type of analysis used in the past test, and the disease name.

Described below is a specific example of the relationship among the test results, the test conditions and/or the disease name, and the content of the setting. In a macula test, settings as follows can be employed: (1) As the fixation position is used a fixation position where the macula is included in the scan range, for example, a fixation position where the macula is located on the extension of the optical axis of the measurement optical path. (2) As the scan pattern, a three-dimensional scan pattern, a radial scan pattern and/or a line scan pattern are/is used. (3) As the focus position is used a focus position applied in the past OCT measurement, or a focus position obtained by calculation from the measurement value (axial length, refractive power, etc.) of the subject's eye E. (4) As the diopter correction is used whether a diopter correction lens is applied in the past OCT measurement, or a diopter correction value obtained from the measurement value of the refractive power of the subject's eye E. (5) As the maximum interference depth is used a maximum interference depth applied in the past OCT measurement, or a maximum interference depth obtained by calculation from the measurement value (axial length, refractive power, etc.) of the subject's eye E. At this time, it is possible to refer to the site of the fundus Ef set as the maximum interference depth (the surface of the fundus, the deep tissue of interest, etc.). (6) As the analysis, the fundus layer thickness analysis (and comparative analysis with the standard layer thickness) is used. In the fundus layer thickness analysis, for example, the thickness of the retina is determined (retinal thickness analysis).

In an optic disc test, settings as follows can be employed: (1) As the fixation position is used a fixation position where the optic disc is included in the scan range, for example, a fixation position where the optic disc is located on the extension of the optical axis of the measurement optical path. (2) As the scan pattern, a three-dimensional scan pattern and/or a circle scan pattern are/is used. (3) As the focus position is used a focus position applied in the past OCT measurement, or a focus position obtained by calculation from the measurement value (axial length, refractive power, etc.) of the subject's eye E. (4) As the diopter correction is used whether a diopter correction lens is applied in the past OCT measurement, or a diopter correction value obtained from the measurement value of the refractive power of the subject's eye E. (5) As the maximum interference depth is used a maximum interference depth applied in the past OCT measurement, or a maximum interference depth obtained by calculation from the measurement value (axial length, refractive power, etc.) of the subject's eye E. At this time, it is possible to refer to the site of the fundus Ef set as the maximum interference depth (the surface of the fundus, the deep tissue of interest such as, for example, retinal nerve fiber layer, etc.). (6) As the analysis, the fundus layer thickness analysis (and comparative analysis with the standard layer thickness) and/or the optic disc shape analysis are/is used. In the fundus layer thickness analysis, for example, the thickness of the retinal nerve fiber layer is obtained (RNFL thickness analysis).

In a glaucoma test, settings as follows can be employed: (1) As the fixation position is used a fixation position where the macula is included in the scan range (e.g., a fixation position where the macula is located on the extension of the optical axis of the measurement optical path), and/or a fixation position where the optic disc is included in the scan range (e.g., a fixation position where the optic disc is located on the extension of the optical axis of the measurement optical path). (2) As the scan pattern, a three-dimensional scan pattern is used. (3) As the focus position is used a focus position applied in the past OCT measurement, or a focus position obtained by calculation from the measurement value (axial length, refractive power, etc.) of the subject's eye E. (4) As the diopter correction is used whether a diopter correction lens is applied in the past OCT measurement, or a diopter correction value obtained from the measurement value of the refractive power of the subject's eye E. (5) As the maximum interference depth is used a maximum interference depth applied in the past OCT measurement, or a maximum interference depth obtained by calculation from the measurement value (axial length, refractive power, etc.) of the subject's eye E. At this time, it is possible to refer to the site of the fundus Ef set as the maximum interference depth (the surface of the fundus, the deep tissue of interest such as, for example, retinal nerve fiber layer, etc.). (6) As the analysis is used the retinal thickness analysis (and comparative analysis with the standard layer thickness), the RNFL thickness analysis (and comparative analysis with the standard layer thickness), and/or the optic disc shape analysis.

In an age-related macular degeneration test, settings as follows can be employed: (1) As the fixation position is used a fixation position where the macula is included in the scan range, for example, a fixation position where the macula is located on the extension of the optical axis of the measurement optical path. (2) As the scan pattern, a three-dimensional scan pattern is used. (3) As the focus position is used a focus position applied in the past OCT measurement, or a focus position obtained by calculation from the measurement value (axial length, refractive power, etc.) of the subject's eye E. (4) As the diopter correction is used whether a diopter correction lens is applied in the past OCT measurement, or a diopter correction value obtained from the measurement value of the refractive power of the subject's eye E. (5) As the maximum interference depth is used a maximum interference depth applied in the past OCT measurement, or a maximum interference depth obtained by calculation from the measurement value (axial length, refractive power, etc.) of the subject's eye E. At this time, it is possible to refer to the site of the fundus Ef set as the maximum interference depth (the surface of the fundus, the deep tissue of interest, etc.). (6) As the analysis, the retinal thickness analysis (and comparative analysis with the standard layer thickness), and/or drusen analysis are/is used.

Part or all of the setting information can be created automatically. In this case, the main controller 111 or the external computer 1000 acquires the test results and the test conditions of the subject's eye E as well as information about the disease name from the electronic medical records of the subject. Then, the setting information is created to include the information thus acquired.

(Authorized User Authentication Information)

The authorized user authentication information is authentication information for the user (authorized subject) who has been allowed to perform a test by using the ophthalmologic imaging apparatus 1. The user authentication information is information used to authenticate a user who is going to perform a test by using the ophthalmologic imaging apparatus 1.

Character string information or image information is used as the user authentication information. Examples of the character string information include a patient ID assigned in the medical institution, personal information such as the name of the subject, a character string arbitrarily specified by the subject, and a character string specified randomly. Examples of the image information include biometric information (a fingerprint pattern, an iris pattern, a vein pattern, a face-type pattern, etc.), a one-dimensional code, and a two-dimensional code. A voice pattern and a handwriting pattern can also be used as the user authentication information.

The authorized user authentication information is input to the ophthalmologic imaging apparatus 1 before, for example, the ophthalmologic imaging apparatus 1 is lent to the subject. When the authorized user authentication information is a character string, it is input manually using the user interface 200 or the external computer 1000, read by using a reader such as a card reader, read from the electronic medical record, or the like. When the authorized user authentication information is image information, it is read by using a reader such as a card reader, input by scanning information written on a paper sheet, read from the electronic medical record or the like, input from a biometric authentication information input device (fingerprint scanner, iris scanner, vein scanner, face analyzer, etc.), or the like. Further, when a voice pattern is employed, the authorized user authentication information is input from a voice input device. If a handwriting pattern is employed, the authorized user authentication information is input from a scanner that has read information written on a paper sheet.

A person, who is going to perform a test using the ophthalmologic imaging apparatus 1, enters user authentication information in a predetermined manner. The entry method corresponds to the type of the user authentication information to be used. That is, the user authentication information is entered on the occasion of using the ophthalmologic imaging apparatus 1 in a similar manner to the entry of the authorized user authentication information described above. Constituent units for entering the user authentication information correspond to the second input unit.

Specific examples of the second input unit include the following: the user interface 200 for the manual entry of user authentication information; the communication unit 140 that receives user authentication information entered on the external computer 1000; a reader such as a card reader to read user authentication information recorded on a recording medium such as a card; the communication unit 140 that receives user authentication information recorded on an electronic medical record or the like; a scanner that scans user authentication information written on a paper sheet; a biometric authentication information input device (fingerprint scanner, iris scanner, vein scanner, face analyzer, etc.), or the like that reads user authentication information consisting of biometric authentication information; and a voice input device for inputting user authentication information consisting of audio information When two or more subjects share the ophthalmologic imaging apparatus 1, authorized user authentication information for each of the subjects is stored in the storage 112 in advance.

(Image Forming Unit 120)

An image forming unit 120 generates image data of a two-dimensional cross-sectional image of the subject's eye E based on a detection signal from the CCD image sensor 23. This process includes, as with the conventional spectral-domain OCT, noise removal (noise reduction), filtering, dispersion compensation, fast Fourier transform (FFT), and the like. If another type of OCT is employed, the image forming unit 120 performs a known process according to the type.

The image forming unit 120 includes, for example, a dedicated circuit board and/or a microprocessor. Incidentally, "image data" may be herein identified as "image" based on it.

(Data Processor 130)

The data processor 130 performs various types of data processing. For example, the data processor 130 performs image processing on an image formed by the image forming unit 120. As an example, the data processor 130 can generate image data of a three-dimensional image of the subject's eye E based on a plurality of two-dimensional cross-sectional images of different cross-sections. The image data of a three-dimensional image is image data in which the positions of pixels are defined by the three-dimensional coordinate system. As one example of the image data of a three-dimensional image may be cited image data formed of three-dimensional arrays of voxels. This image data is referred to as volume data or voxel data. When displaying an image based on volume data, the data processor 130 performs rendering on the volume data (volume rendering and maximum intensity projection (MIP), etc.) to generate image data of a pseudo three-dimensional image viewed from a certain sight line direction. The data processor 130 can image an arbitrary cross-section of a three-dimensional image (multi-planar reconstruction (MPR)).

Further, stack data of a plurality of cross-sectional images may be generated as the image data of a three-dimensional image. The stack data is image data obtained by three-dimensionally arranging a plurality of cross-sectional images acquired along a plurality of scan lines based on the positional relationship between the scan lines. That is, the stack data is image data obtained by representing a plurality of cross-sectional images, which have been originally defined by their respective two-dimensional coordinate systems, by a single three-dimensional coordinate system (i.e., embedding them in one three-dimensional space). The data processor 130 is capable of performing MPR based on the stack data.

The data processor 130 includes, for example, a microprocessor, RAM. ROM, a hard disk drive, a circuit board dedicated for predetermined data processing, and the like. A storage device such as a hard disk drive stores in advance a computer program for the microprocessor to perform data processing described below.

The data processor 130 includes a test data generating unit 131, a stationary determination unit 132, a left/right determination unit 133, an authentication processor 134, and a monitoring processor 135.

(Test Data Generating Unit 131)

The test data generating unit 131 processes the detection result of the interference light obtained by the optical unit 10, and thereby generates test data that indicates the state of the subject's eye E. The test data generating unit 131 is an example of a processor. The test data generating unit 131 processes any of the following as the "detection result of the interference light": (1) signal output from the CCD image sensor 23; (2) image data generated by the image forming unit 120; (3) data obtained in the middle of the process performed by the image forming unit 120 (i.e., data obtained in the middle of the image data forming process); and (4) data obtained by processing signals output from the CCD image sensor 23 by a component other than the image forming unit 120

Described below are examples of processing performed by the test data generating unit 131. As a first example, the test data generating unit 131 can generate layer thickness information of the fundus Ef based on the detection result of the interference light obtained by the optical unit 10. In this case, the test data generating unit 131 functions as a layer thickness information generating unit, and performs the fundus layer thickness analysis (retinal thickness analysis, RNFL thickness analysis, etc.) described above. Further, the test data generating unit 131 may perform the comparative analysis between the layer thickness information obtained by the fundus layer thickness analysis and the standard layer thickness.

The fundus layer thickness analysis is a process for obtaining the thickness (distribution) of a predetermined layer tissue of the fundus Ef based on the detection result of the interference light. The retinal thickness analysis is described as one example thereof. A similar process is performed to determine the thickness of other layer tissues.

In the retinal thickness analysis, for example, a cross-sectional image or a three-dimensional image of the fundus Ef is analyzed to obtain the thickness distribution of the retina in part or all of the scan range. Note that the retinal thickness has different definitions. For example, the retinal thickness may be defined as a thickness from the inner limiting membrane to the inner nuclear layer (inscribed or circumscribed in visual cells), a thickness from the inner limiting membrane to the retinal pigment epithelium, or the like. The retinal thickness obtained by the retinal thickness analysis is defined by one of these definitions.

For example, the retinal thickness analysis is performed in the following manner. First, an OCT image of the fundus Ef is analyzed to specify an image area corresponding to predetermined boundary sites (e.g., the inner limiting membrane and the retinal pigment epithelium). Then, the number of pixels between specified boundary sites is counted to obtain the retinal thickness (distance in the depth direction). For the process of analyzing an OCT image to obtain the thickness of the fundus layer, reference may be had to, for example, Japanese Unexamined Patent Application Publication Nos. 2007-325831, 2008-206684, 2009-61203, and 2009-66015 filed by the present applicant.

The comparative analysis of the retinal thickness is an analysis comparing the retinal thickness obtained by the retinal thickness analysis and normative data stored in advance. The normative data indicates a standard thickness of the retina of the healthy eye. The normative data is created by measuring the retinal thickness of a number of healthy eyes, and obtaining a statistical value of the measurement results (average value, standard deviation, etc.). The comparative analysis determines whether the retinal thickness of the subject's eye E is within the range of that of healthy eyes. Incidentally, when the range of the retinal thickness of eyes with a disease is determined, the comparative analysis may determine whether the retinal thickness obtained by the retinal thickness analysis is within in the range.

The test data generating unit 131 may be configured to be capable of performing the drusen analysis. The drusen analysis is a process of analyzing, for example, an OCT image to obtain the distribution of drusen in part or all of the scan range. The distribution includes the position and size (area, volume, diameter) of the drusen in the eye fundus, and the like.

In the drusen analysis, for example, an OCT image is analyzed to specify an image area corresponding to the Bruch's membrane and an image area corresponding to the retinal pigment epithelium. Then, an image area corresponding to a small substantially circular raised shape is specified as drusen (candidate) based on pixel values between these image areas. The process of specifying the image area based on such a shape can be carried out by, for example, image matching with a template of the shape. Further, the test data generating unit 131 obtains the position, number, size, and the like of drusen based on the image area corresponding to the drusen thus specified. Further, evaluation information can be generated for the state of age-related macular degeneration based on the distribution of the drusen acquired.

Incidentally, when there is provided the front mage acquisition optical system mentioned above and an image of the fundus Ef can be captured, the drusen analysis can be performed based on the captured image of the fundus Ef. In this drusen analysis, for example, it is determined whether the pixel value of each pixel in the captured image falls within a predetermined range to specify pixels in the range. If the captured image is a color image, the drusen is illustrated in a specific color (yellowish white). Accordingly, a range of pixel values corresponding to the specific color is set as the predetermined range in advance. Besides, if the captured image is a monochrome image, drusen is illustrated with characteristic brightness (luminance). Accordingly, a range of pixel values corresponding to the characteristic brightness is set as the predetermined range in advance. Further, an image area corresponding to drusen can be specified by performing template matching based on the standard shape of the drusen (small substantially circular raised shape) or the like.

The optic disc shape analysis may include a process in which a cross-sectional image or a three-dimensional image of the fundus Ef is analyzed to detect a hole (cut, defect site) in the retina to thereby determine the shape of the optic disc. In the optic disc shape analysis, for example, a cross-sectional image or the like is analyzed to specify an image area corresponding to the optic disc and the retinal surface near it. The image area thus specified is analyzed to obtain parameters (optic disc shape parameters) representing the global shape and the local shape (concavity and convexity). Examples of the optic disc shape parameters include the diameter of the cup of the optic disc, the disc diameter, the rim diameter, the depth of the optic disc, and the like.

In addition, the optic disc shape analysis may include a process of obtaining a tilt of the optic disc (asymmetry of the shape). For example, this analysis process is performed in the following manner. First, the test data generating unit 131 analyzes a three-dimensional image obtained by scanning an area including the optic disc to specify the center of the optic disc. Next, the test data generating unit 131 sets a circular area around the center of the optic disc, and divides the circular area radially to obtain a plurality of partial areas. Subsequently, the test data generating unit 131 analyzes a cross-sectional image of the circular area to obtain the height position of a predetermined layer (e.g., the retinal pigment epithelium layer) at each pixel location. Further, the test data generating unit 131 calculates the average value of height positions of the predetermined layer in the partial areas. Next, the test data generating unit 131 compares a pair of average values obtained for a pair of partial areas corresponding to opposite positions with respect to the center of the optic disc to obtain a tilt of the fundus Ef in the opposite directions. The test data generating unit 131 generates tilt distribution information indicating the distribution of the tilt of the fundus Ef in the circular area based on the tilt obtained for a plurality of opposite directions. In addition, evaluation information can be generated for the state of disease based on the tilt distribution information thus generated (and information indicating the standard distribution).

Although the test data described above is based on results of OCT measurement, the test data may include results of other tests. As an example, if the flat panel display 25 can display optotypes (Landolt rings, etc.) for the subjective visual acuity test, the test data generating unit 131 may generate test data that includes results of the subjective visual acuity test.

The subjective visual acuity test is carried out in such a manner that the subject reads the optotypes presented to the subject's eye E. According to a predetermined computer program, the test data generating unit 131 repeats the process of determining whether the response from the subject is correct and the process of determining a visual target to be presented next depending on the determination result. The main controller 111 displays the visual target determined by the test data generating unit 131 on the flat panel display 25. By repeating these processes, the test data generating unit 131 determines the visual acuity value of the subject's eye E, and generates test data including the visual acuity value.

(Stationary Determination Unit 132)

The stationary determination unit 132 determines whether the subject's eye E is substantially stationary based on data acquired by the optical unit 10 (stationary determination). The term "substantially stationary" indicates not only the state where the subject's eye E is stationary, but also the state where the subject's eye E has a level of movement that does not affect OCT measurement. An acceptable range of this movement is arbitrarily set in advance.

Described below are examples of the stationary determination process. As a first example, the stationary determination is made based on the intensity of the return light of the measurement light. The intensity of the return light of the measurement light is maximum when the alignment is correct (because the specular reflection from the cornea is maximum). The intensity of the return light can be obtained by, for example, detecting part of the return light with a photodetector or the like. The stationary determination unit 132 can determine whether the subject's eye E is substantially stationary based on a temporal variation in the intensity of the return light. Besides, the intensity of the return light is affected by the intensity of the interference light. Therefore, the stationary determination unit 132 can make the stationary determination based on a temporal variation in the intensity of a signal from the CCD image sensor 23.

As a second example, when there is provided the front image acquisition optical system mentioned above, the stationary determination can be made in the following manner. First, a moving image of the subject's eye E is captured with the front image acquisition optical system. Thereby, front images (frames) of the subject's eye E are acquired at regular intervals. The stationary determination unit 132 is sequentially fed with the front images and analyzes them to detect a characteristic site of the subject's eye E. This characteristic site is, for example, the pupil (or its center) in an anterior segment image, and the optic disc (or its center), the macula (or its center), a blood vessel, or an affected area in a fundus image. Further, the stationary determination unit 132 monitors changes in the position of the characteristic site in the from image input in time series, and thereby can determine whether the subject's eye E is substantially stationary.

(Left/Right Determination Unit 133)

The left/right determination unit 133 determines whether the subject's eye E is the left eye or the right eye (left-right determination). The left-right determination is made when the test of both the left and right eyes is performed with the ophthalmologic imaging apparatus 1. When only one of the left and right eyes is tested, for example, information that indicates the eye to be tested is the left eye or the right eye is stored in the storage 112 in advance.

Even if the test of only one eye is performed, the left-right determination may be made to prevent the other eye from being accidentally tested. That is, for example, when the left eye is set as a test object, if the subject's eye E is determined to be the right eye as a result of the left-right determination, predetermined notification information may be output. This notification information is, for example, display information displayed on the display 210 or the flat panel display 25, or sound information output from an audio output unit (not illustrated). Besides, when the measurement light contains visible components, the notification may be provided by flashing the measurement light, for example.

Described below are examples of the left-right determination. As a first example, the left-right determination is made based on the control state of the unit driver 10A. This example is applied when the position of the optical unit 10 varies depending on whether the left eye or the right eye is tested. As described above, the optical unit 10 is moved by the unit driver 10A under the control of the main controller 111. Every time the main controller 111 controls the unit driver 10A, it sends the control contents to the left/right determination unit 133. The left/right determination unit 133 determines whether the optical unit 10 is placed in a position for the test of the left eye or a position for the test of the right eye based on the control contents received from the main controller 111. Incidentally, a range of the position for the test of the left eye and a range of the position for the test of the right eye are set in advance.

As a second example, when there is provided the front image acquisition optical system mentioned above, the left-right determination can be made by analyzing a front image. If the front image is an image of the anterior eye segment, the inner corner side and the outer corner side can be identified based on, for example, the shape of the eyelid. Thus, it is possible to determine whether the subject's eye E is the left eye or the right eye. If the front image is an image of the fundus, a determination can be made on whether the subject's eye E is the left eye or the right eye based on the position of the optic disc, the position of the macula, the positional relationship between the optic disc and the macular, the running state of blood vessels, and the like.

As described above, the left/right determination unit 133 has the function of automatically determining whether the subject's eye E is the left eye or the right eye. The determination result is fed to the controller 110. The left/right determination unit 133 functions as a first input unit that feeds the controller 110 with information indicating whether the subject's eye E is the left eye or the right eye. Meanwhile, such an automatic determination function may be dispensed with. For example, the subject (or an assistant) enters whether the subject's eye E is the left eye or the right eye through the operation unit 220. In this case, the operation unit 220 corresponds to the first input unit.

(Authentication Processor 134)

As described above, the controller 110 receives an input of user authentication information from the second input unit. The controller 110 sends the user authentication information to the authentication processor 134 together with the authorized user authentication information stored in the storage 112. The authentication processor 134 determines whether the user authentication information and the authorized user authentication information match. The authentication processor 134 sends the determination result to the controller 110.

When two or more subjects share the ophthalmologic imaging apparatus 1, i.e., when there are two or more authorized subjects, as described above, the authorized user authentication information for each subject is stored in the storage 112. Upon receipt of an input of user authentication information, the controller 110 sends the user authentication information to the authentication processor 134 together with all authorized user authentication information stored in the storage 112. The authentication processor 134 determines whether the user authentication information matches one of pieces of the authorized user authentication information. In other words, the authentication processor 134 searches for authorized user authentication information that matches the user authentication information.

(Monitoring Processor 135)

The monitoring processor 135 monitors the operation state of a predetermined part of the ophthalmologic imaging apparatus 1. For example, the monitoring processor 135 detects a malfunction, damage, failure and the like of the predetermined part of the ophthalmologic imaging apparatus 1. Alternatively, the monitoring processor 135 detects that there is a risk of a malfunction, damage, failure and the like of the predetermined part of the ophthalmologic imaging apparatus 1. As a specific example, the monitoring processor 135 measures the cumulative operation time, and detects that the measurement result exceeds a predetermined threshold.

The part of the ophthalmologic imaging apparatus 1 monitored may include any hardware and/or any software. Examples of the hardware include a microprocessor, RAM, ROM, a hard disk drive, a communication interface, a light source, an optical element, a light receiving element, an actuator, a mechanism, a cable, and the like. Examples of the software include a computer program for apparatus control, a computer program for data processing, and the like.

Described below is an example of a method of monitoring the operation state of the predetermined part. The monitoring processor 135 detects a physical quantity related to monitored hardware. The monitoring processor 135 then determines whether the detection value falls in an acceptable range to thereby determine whether an error occurs in the hardware. Examples of such processing are as follows: to detect heat and determine whether it is equal to or above a predetermined temperature; to detect sound emitted by the mechanism, and determine whether it is abnormal according to the frequency thereof or the like; and to detect the displacement of the hardware with an encoder or the like, and determine whether the abnormal operation of the mechanism or rattling is occurring.

As another example of the monitoring method, predetermined data is entered into the microprocessor. It is possible to determine whether the microprocessor is operating correctly or the computer program is normal depending on whether processed data is normal.

(Communication Unit 140)

The communication unit 140 performs data communication with the external device by an arbitrary method. For example, the communication unit 140 includes a communication interface compatible with the Internet, a communication interface compatible with LAN, and a communication interface compatible with near field communication. The data communication may be wireless or wired communication.

The communication unit 140 performs data communication with the external computer 1000 designated in advance via the communication line 2000. There are provided one or more external computers (1000). Examples of the external computer 1000 include a server installed in the medical institution, a terminal used by a doctor, a server of a manufacturer (or maintenance carrier, rental business, etc.) of the ophthalmologic imaging apparatus 1, a terminal used by the personnel of the manufacturer etc., and the like.

Data transmitted and received by the communication unit 140 may be encrypted. In this case, the controller 110 (or the data processor 130) includes an encryption processor that encrypts transmission data, and a decryption processor that decrypts received data.

[Operation]

Described below is the operation of the ophthalmologic imaging apparatus 1 according to the embodiment.

Figure 3A:
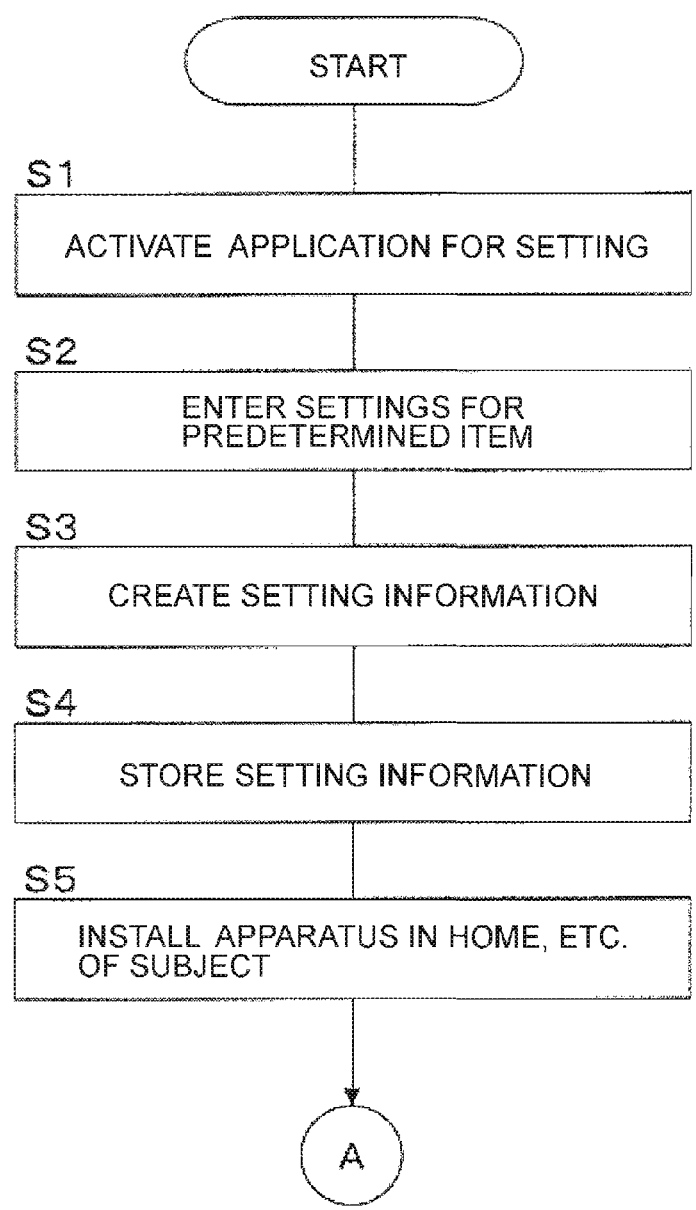
FIG. 3A is a flowchart illustrating an example of the operation of the ophthalmologic imaging apparatus according to an embodiment.
Figure 3B:
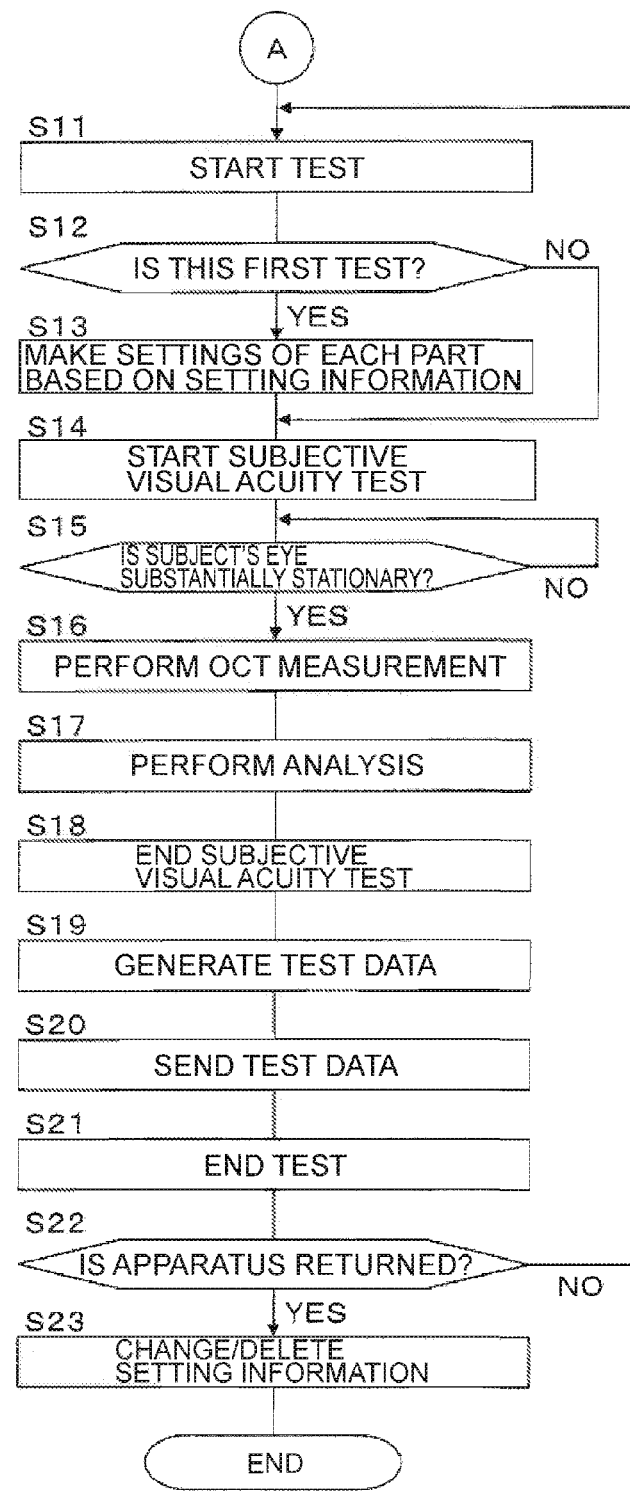
FIG. 3B is a flowchart illustrating an example of the operation of the ophthalmologic imaging apparatus according to an embodiment.

FIGS. 3A and 3B illustrate an example of the operation of the ophthalmologic imaging apparatus 1. In this example, the ophthalmologic imaging apparatus 1 is used in the home or the like of the subject after the settings have been made in a medical institution or the like. The ophthalmologic imaging apparatus 1 is operated by the subject (or his/her assistant). FIG. 3A illustrates the process until the ophthalmologic imaging apparatus 1 is placed in the home or the like of the subject. FIG. 3B illustrates the process from the installation of the ophthalmologic imaging apparatus 1 to the return of it, especially, the usage of the ophthalmologic imaging apparatus 1 in the home or the like of the subject.

(S1: Activate Application for Setting)

First, settings are made as to the operation of the ophthalmologic imaging apparatus 1 in a medical institution or the like. For this, an application program for setting is activated. The application program is installed in the ophthalmologic imaging apparatus 1 or the external computer 1000. As described above, the settings are made by using the ophthalmologic imaging apparatus 1 or the external computer 1000. The application program is installed in an apparatus used to make the settings.

(S2: Enter Settings for Predetermined Item)

Then, a doctor or the like enters the settings for a predetermined item(s) related to the optical unit 10 and the data processor 130 in the manner described above, for example.

(S3: Create Setting Information)

The main controller 111 creates setting information including the settings entered, for example, in the manner described above.

(S4: Store Setting Information)

The main controller 111 stores the setting information created in step S3 in the storage 112, for example, in the manner described above. The setting information include, for example, the setting of the fixation position, the setting of the scan pattern, the setting of the focus position, the setting of the diopter correction, the setting of the analysis process, and the like.

(S5: Install Apparatus in Home, etc. of Subject)

After the completion of the storage of the setting information in step S4, the ophthalmologic imaging apparatus 1 is transported to the home or the like of the subject and installed therein. At this time, a fixture or the like can be used for installing the ophthalmologic imaging apparatus 1 stably. The process from the next step is described referring to FIG. 3B.

(S11: Start Test)

First, an instruction is issued to start the test. This instruction may be made by, for example, turning on the power, pressing a test start button, entering user authentication information, or the like.

The user authentication information is entered in the manner described above, for example. The authentication processor 134 determines whether the user authentication information entered matches authorized user authentication information stored in the storage 112 in advance. The authentication processor 134 sends the determination result to the controller 110. If the user authentication information matches the authorized user authentication information, the test is to be performed. On the other hand, if the user authentication information and the authorized user authentication information do not match, the main controller 111 outputs a message prompting the user to enter user authentication information again by voice or by display. The main controller 111 repeats the output of the message until the determination of mismatch reaches a predetermined number of times (e.g., three times). If the determination of mismatch exceeds the predetermined number, the main controller 111 prohibits the test by the ophthalmologic imaging apparatus 1. Further, the main controller 111 controls the communication unit 140 to notify the external computer 1000 of the prohibition of the test (that an authentication error has occurred). The doctor or the personnel of the manufacturer recognizes the authentication error through the external computer 1000, and performs predetermined operation for canceling the prohibition of the test (check by phone, etc.). The external computer 1000 may be configured to perform the operation for canceling the prohibition of the test. For example, the external computer 1000 sends information for identity verification to a portable terminal or a computer of the subject. A password is entered based on this information. The external computer 1000 determines whether the person who has entered the password is an authorized subject based on the validity of the password. If the person is determined to be an authorized subject, the external computer 1000 sends information for canceling the prohibition of the test to the ophthalmologic imaging apparatus 1. The main controller 111 cancels the prohibition of the test based on the information received from the external computer 1000.

(S12: Is this First Test?)

Upon receipt of an instruction to start the test in step S11, the main controller 111 determines whether this test is the first test after the ophthalmologic imaging apparatus 1 has been installed in the home or the like of the subject. This process can be implemented by, for example, storing a log in the storage 112 each time a test is performed as well as resetting the test log prior to the installation of the apparatus in the home or the like. If this test is determined to be a second or subsequent test (S12: NO), step S13 is skipped and the process moves to step S14. On the other hand, if this test is determined to be the first test (S12: YES), the process moves to step S13.

(S13: Make Setting of Each Part Based on Setting Information)

If this test is determined to be the first test (S12: YES), the main controller 111 makes settings of relevant parts included the optical unit 10 and the data processor 130 based on the setting information stored in the storage 112 in step S4. This process includes, for example, any one or more of the following: to set the display position of a fixation target (or may be a visual target for subjective visual acuity test) on the flat panel display 25 based on the setting of the fixation position; to set the control content of the scanner 16 based on the setting of the scan pattern; to control the movement of the objective lens 19 based on the setting of the focus position; to control the movement of the diopter correction lens 27 based on the setting of the diopter correction; to control the movement of the reference mirror 14 based on the setting of the maximum interference depth; to select the operation of the test data generating unit 131 (i.e., a computer program to be used) based on the setting of analysis process; and the like.

Note that, as can be seen from the flow of the operation illustrated in FIG. 3B, in each test performed until the setting information is changed or deleted in step S23, the settings made in step S13 are applied.

At any timing after the storage of the setting information in step S4, settings may be made for each part based on the setting information. For example, the settings may be made before the ophthalmologic imaging apparatus 1 is transported to the home or the like of the subject. However, taking into account the case where a shift occurs in the settings during the transportation, the settings are made after the transportation in this example. A shift is likely to occur particularly in the arrangement of optical elements. Therefore, settings for others (the setting of the fixation position, the setting of the scan pattern, the setting of the analysis process) may be made before the transportation.

Further, in addition to the settings made in step S13, automatic alignment, automatic focusing (fine adjustment of the focus position), automatic tracking, fine adjustment of the maximum interference depth, light amount adjustment, polarization adjustment, and the like may be performed. The automatic alignment, automatic focusing, and automatic tracking are carried out in the manner described above. The fine adjustment of the maximum interference depth may be performed by, for example, specifying the position of a predetermined site (surface of the fundus, the retinal nerve fiber layer, etc.) of the fundus Ef from a moving image of a cross-sectional image obtained by repeatedly performing a line scan, and adjusting the position of the reference mirror 14 such that the predetermined site is located in a predetermined position in the frame. Further, the light amount adjustment is performed by controlling an optical attenuator, and the polarization adjustment is performed by controlling a polarization adjuster.

(S14: Start Subjective Visual Acuity Test)

In this example, OCT measurement and subjective visual acuity test are performed as the test for the subject's eye E. More specifically, the OCT measurement is performed in the middle of the subjective visual acuity test. In this case, the main controller 111 first starts the subjective visual acuity test. That is, the first visual target is presented to the subject's eye based on the optometry program determined in advance.

At this time, the main controller 111 can display the visual target for the subjective visual acuity test at a display position on the flat panel display 25 based on the setting of the fixation position included in the setting information. For example, if the Landolt ring, which is a circle with a break in it, is used as the visual target, the Landolt ring can be displayed such that the break is located at a position according to the setting of the fixation position. More generally, the visual target can be displayed on the flat panel display 25 such that a part of the visual target that the subject is particularly interested in is placed at a position according to the setting of the fixation position. Thereby, the visual target for subjective visual acuity test can be assigned a function as a fixation target for performing OCT measurement.

(S15: Is Subject's Eye Substantially Stationary?)

In response to the start of the subjective visual acuity test, the main controller 111 starts the stationary determination process of the subject's eye E. The stationary determination process is performed, for example, in the manner described above, by the stationary determination unit 132. The stationary determination process is performed until at least it is determined that the subject's eye E is substantially stationary (S15: NO). If it is determined that the subject's eye E is substantially stationary (S15: YES), the process moves to step S16.

If the subject's eye E cannot be determined to be stationary even after a predetermined time has elapsed from the start of the subjective visual acuity test or even the test has progressed to a predetermined stage, warning can be performed. For example, this warning may be implemented by the main controller 111 that detects the arrival of the warning timing as described above and controls the display 210 or the audio output unit.

In this example, the OCT measurement is performed in the middle of the subjective visual acuity test; however, the tests may be performed at arbitrary timing. For example, OCT measurement may be performed after the completion of the subjective visual acuity test, or the subjective visual acuity test may be performed after the OCT measurement.

(S16: Perform OCT Measurement)

In response to that the subject's eye E is determined to be substantially stationary in step S15 (S15: YES), the main controller 111 controls the optical unit 10 to perform the OCT measurement of the subject's eye E. The OCT measurement is performed based on the settings included in the setting information (e.g., the setting of the fixation position, the setting of the scan pattern, the setting of the focus position, the setting of the diopter correction).

(S17: Perform Analysis)

The test data generating unit 131 performs an analysis based on data acquired by the OCT measurement. This analysis is performed based on the setting of the analysis process included in the setting information. Specifically, the test data generating unit 131 performs the fundus layer thickness analysis, drusen analysis, optic disc shape analysis, or the like.

(S18: End Subjective Visual Acuity Test)

In the subjective visual acuity test started in step S14, the visual acuity value of the subject's eye E is determined based on the responses of the subject to visual targets sequentially presented according to the optometry program. The subjective visual acuity test is completed with the determination of the visual acuity. This means that the subjective visual acuity test ends at an arbitrary time after step S14.

(S19: Generate Test Data)

The test data generating unit 131 generates test data including data obtained by the analysis and data obtained by the subjective visual acuity test.

(S20: Send Test Data)

The main controller 111 controls the communication unit 140 to send the test data generated in step S19 to the external computer 1000.

The test data may be accompanied by supplementary information such as the test date, the identification information of the subject and/or the subject's eye E, the identification information of the ophthalmologic imaging apparatus 1, and the like. The test date is obtained by the date and time functions installed in the main controller 111 (system software), for example. Alternatively, information on the test date and time may be provided by the external computer 1000 or the like. Various types of identification information is stored in the storage 112 in advance.

(S21: End Test)

After the test data is sent in step S20, the test is completed. Accordingly, for example, the subject turns the power off.

(S22: Is Apparatus Returned?)

The test as above is repeated until the return of the ophthalmologic imaging apparatus 1 (S22: NO). The ophthalmologic imaging apparatus 1 is returned due to, for example, the end of the test (follow-up, etc.) in the home or the like, replacement of the apparatus, maintenance of the apparatus, a change in the setting information, or the like. In response to the determination to return the ophthalmologic imaging apparatus 1 (S22: YES), the ophthalmologic imaging apparatus 1 is transported to a medical institution or a manufacturer.

(S23: Change/Delete Setting Information)

The doctor in the medical institution or the personnel of the manufacturer changes or deletes the setting information stored in the ophthalmologic imaging apparatus 1. This is the end of the description of this operation example.

(Other Examples of the Operation)

Other examples of the operation of the ophthalmologic imaging apparatus 1 are described focusing on differences from the above operation example.

A doctor or the like instructs the subject to perform a test at a predetermined time interval (e.g. every day, every other day). Information that indicates the time interval or a period longer than it (collectively referred to as "predetermined period") is stored in advance in the storage 112. The main controller 111 monitors the interval between tests actually performed in the home or the like. This process is carried out, for example, with reference to the test log mentioned above. If the test has not been performed for a predetermined period of time, i.e., when test data has not been generated for a predetermined period of time, the main controller 111 controls the communication unit 140 to send notification information to the external computer 1000. The notification information includes information indicating that the test has not been performed for a predetermined period of time.

There is the case where both the left and right eyes are tested at home or the like. In this case, the setting information includes setting information for the left eye and setting information for the right eye. In other words, the settings are entered for both the eyes in step S2 of FIG. 3A, setting information is created to include the setting of both the eyes in step S3, and the setting information including the setting of both the eyes is stored in the storage 112 in step S4. In addition, in step S11, information indicating whether the subject's eye E is the left eye or the right eye is input from the first input unit (the left/right determination unit 133 or the operation unit 220) to the main controller 111. The main controller 111 selects one of the setting information for the left eye and the setting information for the right eye based on the input information, and performs the setting process of step S13 based on the setting information selected. Moreover, in response to the end of the test for the left eye or the right eye based on the setting information (step S18), the main controller 111 outputs a message indicating that the eye to be tested is changed (visual information or audio information). If there are provided binocular eyepieces for respectively receiving the left eye and the right eye, the main controller 111 controls the optical unit 10 to perform the process of switching an object to which the visual target is to be presented and an object to be irradiated with the measurement light. The switching operation is intended to switch the destination, to which light fluxes are to be guided, between the eyepiece for the left eye and the eyepiece for the right eye by driving, for example, a mirror, a polarization element, a wavelength selection element, and the like. Upon completion of the test of both the eyes, test data is generated to include the test results of the eyes in step S19. The test data is sent to the external computer 1000 in step S20. Thereby, the test ends (S21).

There may be a case where two or more subjects share the ophthalmologic imaging apparatus 1. In this case, the storage 112 stores setting information for each of the subjects. In other words, the settings related to each of the subjects are entered in step S2 of FIG. 3A, setting information is created for each of the subjects in step S3, and the setting information is stored in the storage 112 for each of the subjects in step S4. The storage 112 also stores authorized user authentication information for each of the subjects. User authentication information is entered in step S11. The main controller 111 searches for authorized user authentication information that matches the user authentication information entered to specify the setting information corresponding to the authorized user authentication information. The main controller 111 makes settings in step S13 based on the setting information specified.

The test data obtained by the ophthalmologic imaging apparatus 1 can be stored inside the apparatus. Specifically, at timing after step S19, the main controller 111 stores the test data generated in step S19 in the storage 112. At this time, the test data may be stored in association with the test date and time. In addition, information indicating whether the subject's eye E is the left eye or the right eye and identification information of the subject may also be stored in association with the test data.

It may be possible to notify that an error has been detected in the operation of the ophthalmologic imaging apparatus 1. The monitoring processor 135 detects the operation error. As a first example of the notification method, the notification is provided through the external computer 1000. That is, when the monitoring processor 135 has detected the operation error, the main controller 111 controls the communication unit 140 to send information indicating the occurrence of the error to the external computer 1000. As a second example of the notification method, the notification is provided to the subject. That is, when the monitoring processor 135 has detected the operation error, the main controller 111 controls the display 210 and/or the audio output unit to output notification information (visual information and/or audio information) indicating the occurrence of the error. The display 210 and the audio output unit are examples of the information output unit. Such notification process may be performed at any timing. If an error is detected during a test, it may be notified immediately, or may be notified after the completion of the test. Further, the method and timing of notification may vary according to the part where an error has occurred. For example, when an error is detected in the optical unit 10 during a test, the main controller 111 interrupts the test, and immediately notifies both the external computer 1000 and the subject of the error. Besides, when an error is detected in a part related to the analysis process, the main controller 111 proceeds the processing to the step (OCT measurement, subjective visual acuity test) previous to the analysis process, and thereafter, sends notification information to the external computer 1000 together with data acquired.

[Effects]

The ophthalmologic imaging apparatus 1 is an example of an ophthalmologic imaging apparatuses according to an embodiment. Described below are the effects of an ophthalmologic imaging apparatus of an embodiment.

The ophthalmologic imaging apparatus includes an optical system (e.g., the optical unit 10), a processor (e.g., the test data generating unit 131), an output unit (e.g., the display 210 and/or the communication unit 140), an interface (e.g., the communication unit 140 and/or the user interface 200), a storage (e.g., the storage 112), and a controller (e.g., the main controller 111).

The optical system is configured to divide light from a light source (e.g., the light source 11) into measurement light and reference light, and cause the measurement light having passed through a subject's eye to interfere with the reference light, thereby detecting interference light resulting from the interference. The processor is configured to process the detection result of the interference light obtained by the optical system to generate test data indicating the state of the subject's eye. The output unit is configured to output the test data generated by the processor. The interface is used to make the setting of a predetermined item related to the optical system and the processor. The storage is configured to store setting information indicating the content of the setting made through the interface. The controller is configured to control the optical system and the processor based on the content of the setting indicated by the setting information in each of a plurality of tests performed until the setting information is changed or deleted.

With this ophthalmologic imaging apparatus, when setting information that defines the operation of the apparatus is once set, test is performed based on the setting information until the setting information is changed or deleted. Such a configuration is different from that of the conventional ophthalmologic imaging apparatus, which is expected to be installed in a medical institution where the subject's eye changes randomly. Moreover, since each test is performed based on the setting information created in advance, it is not necessary to perform the troublesome setting operation and adjustment operation at the time of each test. Therefore, even those having no or little knowledge and experience about using the apparatus can perform a test with the ophthalmologic imaging apparatus of the embodiment.

According to the embodiment, in addition to the OCT measurement functions as described above, the ophthalmologic imaging apparatus may also have subjective visual acuity test functions. In this case, the optical system includes a flat panel display (e.g., the flat panel display 25) configured to display a visual target for a visual acuity test under the control of the controller. The optical system guides a light flux output from the flat panel display to the subject's eye to present the visual target to the subject's eye. Further, the ophthalmologic imaging apparatus of the embodiment includes an operation unit (e.g., the operation unit 220) for inputting a response of the subject to the visual target presented by the optical system. The processor obtains the visual acuity value of the subject's eye based on the responses input by using the operation unit, and generates test data including the visual acuity value.

The test data includes one or both of test results based on the OCT measurement and results of the subjective visual acuity test. That is, when only the OCT measurement has been performed, the test data includes the former, while when only the subjective visual acuity test has been performed, the test data includes the latter. When both the OCT measurement and the subjective visual acuity test are performed, the test data includes the both.

With this structure, not only the morphological data of the subject's eye obtained by the OCT measurement, functional data can also be obtained through the subjective visual acuity test. Therefore, it is possible to test the state of the subject's eye from a wider angle. In addition, the test can be performed at home or the like. Thus, it is possible to perform medical procedures, such as medication administration, in more appropriate timing.

The setting information may include setting of a fixation position. In this case, the controller can display a fixation target for fixating the subject's eye on the flat panel display based on the setting of the fixation position. Thereby, the OCT measurement can be performed for a site of interest of the subject's eye. Note that the fixation target may be a visual target for the subjective visual acuity test or may be visual target dedicated to fixation.

The controller can control the optical system to detect interference light while performing control to display the visual target on the flat panel display. That is, the OCT measurement can be performed during the subjective visual acuity test. Thus, the test time can be shortened.

According to the embodiment, the ophthalmologic imaging apparatus may include a stationary determination unit (e.g., the stationary determination unit 132) configured to determine whether the subject's eye is substantially stationary based on data optically acquired. In this case, when the stationary determination unit has determined that the subject's eye is substantially stationary, the controller may control the optical system to detect the interference light. That is, the OCT measurement can be performed at the timing when the subject's eye is substantially stationary. Thereby, it is possible to prevent failure of the OCT measurement due to the movement of the subject's eye.

The light source may be configured to output infrared light, and the flat panel display may be configured to output visible light. In this case, the optical system includes a dichroic mirror (e.g., the dichroic mirror 18) configured to combine the optical path of the measurement light based on the infrared light from the light source and the optical path of the visible light output from the flat panel display. The measurement light and the visible light may be guided to the subject's eye through the dichroic mirror. With this configuration, it is possible to carry out the OCT measurement and the presentation of the visual target with coaxial optical systems.

The output unit may include a first communication unit (e.g., the communication unit 140) capable of communicating with a first computer (e.g., external computer 1000) installed in a medical institution via a communication line (the communication line 2000). In this case, the controller may control the first communication unit to send the test data generated by the processor and the identification information of the subject's eye to the first computer. With this configuration, the test data can be sent while clearly identifying the subject's eye. The identification information of the subject's eye may be any information which can identify the subject's eye, and, for example, may be identification information assigned to the subject, the subject's eye, or the ophthalmologic imaging apparatus.

The first communication unit may be capable of communicating with a second computer (e.g., the external computer 1000) installed in a medical institution via a communication line (e.g., the communication line 2000). In this case, when the processor has not generated test data for a predetermined period of time, the controller may control the first communication unit to send notification information to the second computer. With this configuration, the medical institution side can be notified that the test has not been performed as scheduled. Thus, it is possible to instruct the subject to perform the test according to schedule.

When both eyes of a subject are tested by using the ophthalmologic imaging apparatus, setting information for both the eyes may be selectively used. For example, the ophthalmologic imaging apparatus of the embodiment include a first input unit (e.g., the operation unit 220 or the left/right determination unit 133) configured to feed the controller with information indicating whether the subject's eye is the left eye or the right eye. The storage stores, as the setting information, setting information for the left eye related to the left eye of a subject, and setting information for the right eye related to the right eye. The controller selects one of the setting information for the left eye and the setting information for the right eye based on the information input by the first input unit, and controls the optical system and the processor based on the setting information selected. With this configuration, it is possible to carry out the test of both eyes using suitable setting conditions corresponding to each eye.

It may be automatically determined whether an eye to be tested is the left eye or the right eye. For example, the first input unit may include a left/right determination unit (e.g., the left/right determination unit 133) configured to determine whether an eye to be tested is the left eye or the right eye, and feeds the controller with the determination result. In this case, the controller selects one of the setting information for the left eye and the setting information for the right eye based on the determination result fed by the left/right determination unit, and controls the optical system and the processor based on the setting information selected. With this configuration, there is no need to manually set whether the subject's eye is the left eye or the right eye.

The ophthalmologic imaging apparatus may have the function of authenticating the subject. For example, the storage stores in advance authorized user authentication information about an authorized subject who is allowed to perform a test by using the ophthalmologic imaging apparatus. In addition, the ophthalmologic imaging apparatus of the embodiment may include a second input unit (e.g., the operation unit 220, a reader, a biometric authentication information input device) configured to feed user authentication information to the controller, and an authentication processor (e.g., the authentication processor 134) configured to determine whether the user authentication information fed and the authorized user authentication information match. Further, if the authentication processor determines that the user authentication information and the authorized user authentication information do not match, the controller can prohibit the operation of the optical system and the processor. On the other hand, when the user authentication information and the authorized user authentication information are determined to match, the optical system and the processor are controlled based on the setting information to perform a test. With this configuration, only the authorized subject can use the apparatus.

A plurality of subjects may share the ophthalmologic imaging apparatus. For example, the storage stores, for each of two or more authorized subjects, authorized user authentication information and setting information in association with each other. The authentication processor determines whether the storage stores the authorized user authentication information that matches the user authentication information fed by the second input unit. If it is determined that the authorized user authentication information that matches the user authentication information is stored, the controller controls the optical system and the processor based on the setting information associated with the authorized user authentication information. With this configuration, a plurality of subjects can share the ophthalmologic imaging apparatus, and also the test can be carried out by selectively using the setting information for each subject with accuracy.

The setting information of the optical system may include the setting of the scan pattern. In this case, the optical system includes a scanner (e.g., the scanner 16) configured to scan the subject's eye with the measurement light. When performing the OCT measurement, the controller can control the scanner based on the setting of the scan pattern included in the setting information. With this configuration, it is possible to perform the OCT measurement using a suitable scan pattern set in advance for the subject's eye.

The setting information of the optical system may include the setting of the focus position in the OCT measurement. In this case, the optical system includes a focus position change unit configured to change the focus position of the measurement light. The controller controls the focus position change unit based on the setting of the focus position included in the setting information. With this configuration, the OCT measurement can be performed in a suitable focus state set in advance for the subject's eye.

The focus position change unit may include a focusing lens (e.g., the objective lens 19 and/or another focusing lens) provided to the optical system and a first driver (e.g., the lens barrel driver 19B) configured to move the focusing lens along the optical axis. In this case, the setting information includes information indicating the position of the focusing lens. The controller controls the first driver to position the focusing lens in the position indicated by the setting information. Thereby, the focus position of the measurement light can be automatically adjusted. Further, when the objective lens 19 is used as the focusing lens, it is possible to reduce the number of optical elements provided in the optical system, and thus simplify the configuration of the optical system.

In addition, the focus position change unit may include a diopter correction lens (e.g., the diopter correction lens 27) and a second driver (e.g., the lens driver 27A) configured to insert/remove the diopter correction lens into/from the optical system. In this case, the setting information includes information indicating whether the diopter correction lens is to be used. If the setting information indicates that the diopter correction lens is to be used, the controller controls the second driver to insert the diopter correction lens into the optical system. Thereby, diopter correction can be performed automatically according to the refractive index of the subject's eye.

The setting information of the optical system may include the setting of the maximum interference depth where the intensity of the interference between the measurement light and the reference light is the maximum. In this case, the optical system includes a maximum interference depth change unit (e.g., the reference mirror 14 and the reference mirror driver 14A) configured to change the maximum interference depth. The controller controls the maximum interference depth change unit based on the setting of the maximum interference depth. Thereby, the maximum interference depth can be adjusted automatically.

If the setting information of the optical system includes the setting of the maximum interference depth, the following configuration can be employed: The optical system includes a beam splitter (e.g., the beam splitter 13), a measurement arm, and a reference arm. The beam splitter splits light from the light source into measurement light and reference light. The measurement arm corresponds to a measurement optical path that guides the measurement light to the subject's eye and guides the measurement light returning from the subject's eye to the beam splitter. The reference arm corresponds to a reference optical path that includes a mirror (e.g., the reference mirror 14) configured to reflect the reference light toward the beam splitter. The optical system detects the interference light between the reference light and return light of the measurement light obtained through the beam splitter. The maximum interference depth change unit includes the above-mentioned mirror (e.g., the reference mirror 14) and a third driver (e.g., the reference mirror driver 14A) configured to move the mirror in the direction of the optical axis of the reference arm. The setting of the maximum interference depth may include information indicating the position of the mirror. The controller controls the third driver to position the mirror in the position indicated by the setting information. With this configuration, the maximum interference depth can be adjusted by changing the length of the reference optical path depending on the setting of the maximum interference depth. Incidentally, the optical system may be configured to guide light (at least one of the light from the light source, the measurement light, the reference light, and the interference light) using an optical fiber. In addition, there may be provided a mechanism for changing the length of the measurement optical path.

The setting information of the processor may include settings for performing a desired analysis. In this case, the setting information includes the content of processing performed by the processor (e.g., the test data generating unit 131). For example, the processor may include a layer thickness information generating unit (e.g., the test data generating unit 131) configured to generate layer thickness information of the fundus based on the detection result of the interference light obtained by the optical system. If the setting information includes a process of generating the layer thickness information as the content of processing performed by the processor, the controller controls the layer thickness information generating unit to generate the layer thickness information as the test data. Thus, the fundus layer thickness analysis is performed. The same applies to other analyses, such as drusen analysis and optic disc shape analysis. With this configuration, desired analysis can be selectively performed.

Each time the processor generates test data, the controller may store the test data in the storage (e.g., the storage 112) in association with date information. Thereby, the test date and the test data (log or history of tests) can be accumulated in the ophthalmologic imaging apparatus. When this configuration is employed, the accumulated data can be sent to an external device (e.g., the external computer 1000) all together.

According to the embodiment, the operating state of the ophthalmologic imaging apparatus can be remotely monitored. For example, the ophthalmologic imaging apparatus of the embodiment includes a monitoring unit (e.g., the monitoring processor 135) configured to monitor the operation state of a predetermined part. The output unit includes a second communication unit (e.g., the communication unit 140) capable of communicating with a third computer (e.g., the external computer 1000) through a communication line (e.g., the communication line 2000). When the monitoring unit detects an operation error, the controller controls the second communication unit to send information indicating the occurrence of the error to the third computer. With this configuration, it is possible to provide a notification that an error has occurred in the ophthalmologic imaging apparatus through the external computer 1000.

The subject or his/her assistant may be notified of the occurrence of the error. For example, the ophthalmologic imaging apparatus of the embodiment includes an information output unit (e.g., the display 210 and/or the audio output unit) configured to output visual information and/or audio information. When the monitoring unit detects an operation error, the controller controls the information output unit to output notification information indicating the error. With this configuration, the subject or the like can be notified of that an error has occurred in the ophthalmologic imaging apparatus. Thus, it is possible to cancel the test, contact with the contact personnel, or the like.

The ophthalmologic imaging apparatus of the embodiment may be configures as follows: The optical system (e.g., the optical unit 10) includes a fixation target presenting unit configured to present a fixation target for fixating the subject's eye. The fixation target presenting unit may be, for example a flat panel display (the flat panel display 25). The setting information includes the setting of the fixation position. The controller (e.g., the main controller 111) controls the fixation target presenting unit to present the fixation target based on the setting of the fixation position. With this configuration, it is possible to perform the OCT measurement of the site of interest of the subject's eye.

The configurations described above are mere examples for embodying or carrying out the present invention, and therefore susceptible to several modifications and variations (omission, substitution, addition, etc.), all coming within the scope of the invention.

For example, if the use of the ophthalmologic imaging apparatus of the embodiment involves charging of fees, information related to the fees may be sent to the external computer, or stored in the ophthalmologic imaging apparatus.

As the former example, each time performing a test, the ophthalmologic imaging apparatus may send information indicating the type of the test (e.g., OCT measurement, analysis, subjective visual acuity test) via a communication line to a computer (a hospital information system (HIS), etc.) installed in a medical institution together with patient identification information. This process is performed, for example, in such a manner that the main controller 111 creates the information to be sent and controls the communication unit 140 to send the information to the computer. In the medical institution, based on the information received from the ophthalmologic imaging apparatus, insurance points related to tests performed using the ophthalmologic imaging apparatus and the expenses of a patient are calculated to generate receipt information for the patient.

As the latter example, each time performing a test, the ophthalmologic imaging apparatus stores the type of the test (and examination date, etc.). This process is performed, for example, in such a manner that the main controller 111 creates the information to be stored and stores it in the storage 112. Further, the ophthalmologic imaging apparatus outputs the information stored at a predetermined timing. The output timing may be, for example, when there is a request from a computer in the medical institution, when the ophthalmologic imaging apparatus is returned, or the like. The ophthalmologic imaging apparatus may output the information on a predetermined date (e.g., every Monday, first Monday in every month). The information may be output through a communication line, as being recorded on a portable storage medium (e.g., semiconductor memory), as being printed on a recording sheet medium, or the like. In the medical institution, based on the output information, insurance points related to tests performed using the ophthalmologic imaging apparatus and the expenses of a patient are calculated to generate receipt information for the patient.

A computer program for realizing the above embodiment may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

The invention claimed is:

1. An ophthalmologic imaging apparatus comprising:
   an optical system configured to divide light from a light source into measurement light and reference light, cause the measurement light returning from a subject's eye to interfere with the reference light, and detect interference light resulting therefrom;
   a processor configured to process a detection result of the interference light obtained by the optical system to generate test data indicating a state of the subject's eye;
   an output unit configured to output the test data generated by the processor;
   an interface used to make setting of a predetermined item related to the optical system and the processor;
   a storage configured to store setting information indicating content of the setting made through the interface; and
   a controller configured to control the optical system and the processor based on the content of the setting indicated by the setting information in each of a plurality of tests performed until the setting information is changed or deleted.

2. The ophthalmologic imaging apparatus according to claim 1, wherein
   the optical system includes a fixation target presenting unit configured to present a fixation target for fixating the subject's eye,
   the setting information includes setting of a fixation position, and
   the controller is configured to control the fixation target presenting unit to present the fixation target based on the setting of the fixation position.

3. The ophthalmologic imaging apparatus according to claim 2, wherein the optical system includes a flat panel display as the fixation target presenting unit, and is configured to guide a light flux output from the flat panel display to the subject's eye to present the fixation target to the subject's eye.

4. The ophthalmologic imaging apparatus according to claim 3, wherein
   the light source is configured to output infrared light,
   the flat panel display is configured to output visible light,
   the optical system includes a dichroic mirror configured to combine an optical path of the measurement light based on the infrared light from the light source and an optical path of the visible light output from the flat panel display, and
   the optical system guides the measurement light and the visible light to the subject's eye through the dichroic mirror.

5. The ophthalmologic imaging apparatus according to claim 1, further comprising a stationary determination unit configured to determine whether the subject's eye is substantially stationary based on data optically acquired,
   wherein, when the stationary determination unit has determined that the subject's eye is substantially stationary, the controller controls the optical system to detect the interference light.

6. The ophthalmologic imaging apparatus according to claim 1, wherein
   the output unit includes a first communication unit capable of communicating with a first computer installed in a medical institution via a communication line, and
   the controller is configured to control the first communication unit to send the test data generated by the processor and identification information of the subject's eye to the first computer.

7. The ophthalmologic imaging apparatus according to claim 6, wherein
   the first communication unit is capable of communicating with a second computer installed in the medical institution via the communication line, and
   when the processor has not generated the test data for a predetermined period of time, the controller controls the first communication unit to send notification information to the second computer.

8. The ophthalmologic imaging apparatus according to claim 1, further comprising a first input unit configured to feed the controller with information indicating whether the subject's eye is left eye or right eye,
   wherein the storage stores, as the setting information, left eye setting information related to the left eye of a subject, and right eye setting information related to the right eye, the controller is configured to select one of the left eye setting information and the right eye setting information based on the information fed by the first input unit, and the controller is configured to control the optical system and the processor based on the setting information selected.

9. The ophthalmologic imaging apparatus according to claim 8, wherein the first input unit includes a left/right determination unit configured to determine whether the subject's eye is the left eye or the right eye, and feed determination result to the controller, the controller is configured to select one of the left eye setting information and the right eye setting information based on the determination result fed by the left/right determination unit, and the controller is configured to control the optical system and the processor based on the setting information selected.

10. The ophthalmologic imaging apparatus according to claim 1, wherein the storage stores, in advance, authorized user authentication information about an authorized subject who is allowed to perform a test by using the ophthalmologic imaging apparatus, the ophthalmologic imaging apparatus further comprises:
a second input unit configured to feed user authentication information to the controller; and
an authentication processor configured to determine whether the user authentication information fed by the second input unit and the authorized user authentication information match, and when the authentication processor determines that the user authentication information and the authorized user authentication information do not match, the controller prohibits operation of the optical system and the processor.

11. The ophthalmologic imaging apparatus according to claim 10, wherein the storage stores, for each of two or more authorized subjects, the authorized user authentication information and the setting information in association with each other, the authentication processor is configured to determine whether authorized user authentication information that matches the user authentication information fed by the second input unit is stored in the storage, and when it is determined that authorized user authentication information that matches the user authentication information is stored in the storage, the controller controls the optical system and the processor based on the setting information associated with the authorized user authentication information.

12. The ophthalmologic imaging apparatus according to claim 1, wherein the optical system includes a scanner configured to scan the subject's eye with the measurement light, the setting information includes setting as to a scan pattern with the measurement light, and the controller is configured to control the scanner based on the setting as to the scan pattern.

13. The ophthalmologic imaging apparatus according to claim 1, wherein the optical system includes a focus position change unit configured to change a focus position of the measurement light with respect to the subject's eye, the setting information includes setting as to the focus position of the measurement light, and the controller is configured to control the focus position change unit based on the setting as to the focus position.

14. The ophthalmologic imaging apparatus according to claim 13, wherein the focus position change unit includes a focusing lens of the optical system, and a first driver configured to move the focusing lens, the setting information includes information indicating a position of the focusing lens, and the controller is configured to control the first driver to position the focusing lens in the position indicated by the setting information.

15. The ophthalmologic imaging apparatus according to claim 14, wherein the focusing lens is an objective lens.

16. The ophthalmologic imaging apparatus according to claim 13, wherein the focus position change unit includes a diopter correction lens, and a second driver configured to insert and remove the diopter correction lens in and from the optical system, the setting information includes information indicating whether the diopter correction lens is to be used, and when the setting information indicates that the diopter correction lens is to be used, the controller controls the second driver to insert the diopter correction lens into the optical system.

17. The ophthalmologic imaging apparatus according to claim 1, wherein the optical system includes a maximum interference depth change unit configured to change a maximum interference depth where intensity of interference between the measurement light and the reference light is maximum, the setting information includes setting of the maximum interference depth, and the controller is configured to control the maximum interference depth change unit based on the setting of the maximum interference depth.

18. The ophthalmologic imaging apparatus according to claim 17, wherein the optical system includes:
a beam splitter configured to split the light from the light source into the measurement light and the reference light;
a measurement arm configured to guide the measurement light to the subject's eye and guides the measurement light returning from the subject's eye to the beam splitter; and
a reference arm including a mirror configured to reflect the reference light toward the beam splitter, the optical system is configured to detect the interference light between the reference light and return light of the measurement light obtained through the beam splitter, the maximum interference depth change unit includes the mirror, and a third driver configured to move the mirror along a direction of an optical axis of the reference arm, the setting information includes information indicating a position of the mirror, and the controller is configured to control the third driver to position the mirror in the position indicated by the setting information.

19. The ophthalmologic imaging apparatus according to claim 1, wherein the processor includes a layer thickness information generating unit configured to generate layer thickness information of fundus of the subject's eye based on the detection result of the interference light obtained by the optical system, the setting information includes content of processing performed by the processor, and when the content of the processing performed by the processor includes generation of layer thickness information, the controller controls the layer thickness information generating unit to generate the layer thickness information as the test data.

20. The ophthalmologic imaging apparatus according to claim 1, wherein each time the processor generates test data, the controller stores the test data in the storage in association with date information.

21. The ophthalmologic imaging apparatus according to claim 1, further comprising a monitoring unit configured to monitor operation of a predetermined part of the apparatus, wherein the output unit includes a second communication unit capable of communicating with a third computer through a communication line, and when the monitoring unit detects an error in the operation, the controller controls the second communication unit to send information indicating occurrence of the error to the third computer.

* * * * *